US009517189B2

(12) United States Patent
Arditty et al.

(10) Patent No.: US 9,517,189 B2
(45) Date of Patent: Dec. 13, 2016

(54) COSMETIC COMPOSITION COMPRISING AN OIL, HYDROPHOBIC SILICA AEROGEL PARTICLES AND A HYDROCARBON-BASED RESIN

(71) Applicant: L'OREAL, Paris (FR)

(72) Inventors: Stephane Arditty, Paris (FR); Frederic Auguste, Chevilly la Rue (FR); Virginie Perez Nowak, L'Hay les Roses (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/404,128

(22) PCT Filed: Jun. 21, 2013

(86) PCT No.: PCT/EP2013/063076
§ 371 (c)(1),
(2) Date: Nov. 26, 2014

(87) PCT Pub. No.: WO2013/190132
PCT Pub. Date: Dec. 27, 2013

(65) Prior Publication Data
US 2015/0147366 A1    May 28, 2015

(30) Foreign Application Priority Data
Jun. 21, 2012   (FR) ..................... 12 55881

(51) Int. Cl.
*A61K 8/25*      (2006.01)
*A61K 8/31*      (2006.01)
*A61Q 1/04*      (2006.01)
*A61Q 1/06*      (2006.01)
*A61K 8/81*      (2006.01)
*A61K 8/02*      (2006.01)

(52) U.S. Cl.
CPC ............... *A61K 8/25* (2013.01); *A61K 8/0279* (2013.01); *A61K 8/31* (2013.01); *A61K 8/8117* (2013.01); *A61Q 1/04* (2013.01); *A61Q 1/06* (2013.01); *A61K 2800/30* (2013.01); *A61K 2800/31* (2013.01); *A61K 2800/412* (2013.01)

(58) Field of Classification Search
None
See application file for complete search history.

(56) References Cited

U.S. PATENT DOCUMENTS

| 2005/0187128 | A1* | 8/2005 | Martin | A61K 8/19 |
| | | | | 510/392 |
| 2011/0002864 | A1* | 1/2011 | Ilekti | A61K 8/31 |
| | | | | 424/64 |
| 2011/0195100 | A1 | 8/2011 | Bruning et al. | |
| 2013/0177617 | A1 | 7/2013 | Bruning et al. | |

FOREIGN PATENT DOCUMENTS

| EP | 1 559 393 A1 | 8/2005 |
| EP | 2 263 640 A1 | 12/2010 |
| EP | 2 353 578 A2 | 8/2011 |

OTHER PUBLICATIONS

International Search Report issued Aug. 27, 2014 in PCT/EP2013/063076 filed Jun. 21, 2013.
"Dow Corning VM-2270 Aerogel Fine Particles" Internet Citation, Dow Corning, Product Information Personal Care, XP002650585, Apr. 2009, pp. 1-5, http://www2.dowcorning.com/DataFiles/090007c88020e235.pdf.
U.S. Appl. No. 14/401,735, filed Nov. 17, 2014, Julien, et al.
U.S. Appl. No. 14/408,344, filed Dec. 16, 2014, Arditty, et al.
U.S. Appl. No. 14/401,611, filed Nov. 17, 2014, Perez-Nowak, et al.
U.S. Appl. No. 14/404,980, filed Dec. 2, 2014, Arditty, et al.

* cited by examiner

*Primary Examiner* — Robert A Wax
*Assistant Examiner* — Melissa Mercier
(74) *Attorney, Agent, or Firm* — Oblon, McClelland, Maier & Neustadt, L.L.P.

(57) ABSTRACT

The present invention relates to a cosmetic composition for making up and/or caring for the skin and/or the lips, comprising, in a physiologically acceptable medium, at least one oil, which is preferably non-volatile, at least hydrophobic silica aerogel particles, at least one hydrocarbon-based resin having a number-average molecular weight of less than or equal to 10 000 g/mol, the said composition comprising less than 5% by weight of water relative to the total weight of the composition, and preferably being anhydrous.

26 Claims, No Drawings

COSMETIC COMPOSITION COMPRISING AN OIL, HYDROPHOBIC SILICA AEROGEL PARTICLES AND A HYDROCARBON-BASED RESIN

The present invention relates to a cosmetic composition for making up and/or caring for the skin and/or the lips, comprising hydrophobic silica aerogel particles, at least one oil and at least one hydrocarbon-based resin.

The development of liquid compositions dedicated to making up and/or caring for the skin and/or the lips, especially the lips, such as lip glosses (liquid lip compositions), which are stable and endowed with satisfactory properties in terms of application (glidance on application, and ease of spreading) and also in terms of the makeup effect of the deposit on the lips, for instance the gloss and/or the gloss remanence or the colour remanence, preferably without becoming tacky, is an ongoing objective.

In general, makeup formulations, and in particular those corresponding to liquid or fluid presentation forms, for example of "gloss" type in the case of lip compositions, conventionally comprise fillers, such as silica, and in particular nanosilicas, inter alia, to thicken the composition and to obtain a fluid and stable texture, which may be readily and uniformly applied to the skin or the lips.

Specifically, in the case of fluid (liquid) compositions that especially have, in point of fact, the advantage of enabling the use of large amounts of oils, it is necessary to find a means for thickening these oils in order to obtain a texture that is stable over time and of intermediate viscosity, i.e. which is not too liquid (since it would then be difficult to apply and/or would risk running and/or migrating into the wrinkles and fine lines around the lips), and which is not too thick either, since it would then prove to be difficult to spread on the skin and/or the lips. It is also sought to obtain a composition whose deposition on the skin or the lips does not give rise to a greasy sensation (in the case of an excessively oily deposit) or a sensation of dryness or tautness (in the case of a dry deposit).

In the case of compositions for making up the lips, one of the properties conventionally sought is gloss. Oils, and in particular oils with a high refractive index and/or a high viscosity, are preferred. In particular, liquid (fluid) formulations, of "gloss" type, more particularly known as "liquid gloss" or "lip gloss", are favoured for affording an optimized gloss effect. It is therefore necessary to find a means for thickening these oils without impairing this gloss effect.

In general, the starting materials, and in particular the fillers, conventionally used at the present time for sufficiently thickening a composition, in particular for holding the pigments and nacres in suspension, are "nanosilicas" (the term "nanosilicas" means particles of nanometric size or comprising at least a fraction of nanometric size), generally chosen from the fumed silica particles of INCI name Silica Dimethyl Silylate, which may be hydrophilic- or hydrophobic-treated, for example such as the compound sold under the reference Aerosil® R 972 by Evonik Degussa.

The use of nanosilicas also generally makes it possible to obtain optimized application properties such as destructuring under the effect of the shear generated by the application, which makes it possible to deposit the product uniformly onto the lips, followed by restructuring of the deposit after application, allowing satisfactory remanence of the cosmetic result, and/or making it possible to prevent or limit the unaesthetic migration of the product into the fine lines around the lips. Thus, standard makeup compositions, and in particular lip glosses, conventionally comprise between 2% and 7% by weight of nanosilicas (often hydrophobic-treated), in order to efficiently thicken the oils.

However, when an attempt is made to dispense with the "nanosilicas", it becomes very difficult to obtain a good compromise in terms of gelation of the oils. Specifically, a composition that is not sufficiently thickened and/or gelled will not display good hold of the nacres and pigments, and will have a strong tendency to migrate into the fine lines around the lips. Conversely, an excessively thickened and/or gelled composition will not have good cosmetic properties, especially on application (it will be difficult to deposit uniformly on the lips) and will have low gloss, due to the poor availability of the oils, in particular of the non-volatile oils.

Moreover, these compositions very often conventionally display a tacky and/or pasty nature, which may especially be induced by the presence of high-viscosity oils that are insufficiently gelled (the tacky nature being reflected especially by the made-up lips adhering together, which is unpleasant in terms of comfort for the user) or by excessive thickening of the oils (the oils that have been too greatly thickened then forming a paste which lacks creaminess).

An alternative means to the "nanosilicas" used hitherto is thus sought, to obtain a makeup and/or care composition, in particular a makeup composition, in which the oils are sufficiently gelled and/or thickened, so as not to have the drawbacks mentioned previously, in particular a composition which is stable and which has good spreading properties and whose deposit on the skin and/or the lips, in particular on the lips, is glossy and/or non-migrating.

Preferably, it is also sought to obtain compositions whose deposition on the skin and/or the lips does not have any tacky nature. Specifically, the deposits obtained with liquid formulations comprising a large amount of oil, in particular in the case of liquid compositions such as lip glosses, very often have a tacky nature, caused in particular by the use of these oils, this tacky nature reflected especially by the made-up lips adhering together, which is thus unpleasant in terms of comfort for the user.

Preferably, it is also sought to obtain a composition whose deposit on the skin and/or the lips has a good level of gloss remanence and/or of colour remanence, and preferably which does not transfer onto a cup or an item of clothing, for example.

The inventors have observed, surprisingly, that the use of a combination of hydrophobic silica aerogel particles and of at least one hydrocarbon-based resin with oils makes it possible to obtain liquid cosmetic compositions, which are stable, which have good application properties and whose deposit shows satisfactory gloss, is comfortable (no greasy, pasty and/or dry feel), sparingly migrating or non-migrating and/or is sparingly tacky.

Thus, according to one of its aspects, the present invention is directed towards a cosmetic composition, preferably for making up and/or caring for the skin and/or the lips, preferably in liquid form, comprising, in a physiologically acceptable medium, at least one fatty phase comprising:
  at least one hydrocarbon-based resin, preferably having a number-average molecular weight of less than or equal to 10 000 g/mol,
  at least hydrophobic silica aerogel particles,
  at least one oil, which is preferably non-volatile,
  the said composition comprising less than 5% by weight of water relative to the total weight of the composition, and preferably being anhydrous.

The inventors have in fact observed, surprisingly, that such a cosmetic composition for making up and/or caring for the lips or the skin has satisfactory properties in terms of stability and ease of application, especially of spreading, and the deposit obtained on the skin and/or the lips is homogeneous, glossy and shows good remanence, preferably no transfer, while at the same time not having an exacerbated tacky and/or migrating nature.

Moreover, the composition according to the invention is homogeneous and stable at room temperature. The term "stable" composition especially means that the composition does not undergo any phase separation or exudation, especially after 72 hours or even 1 month at 42° C.

Moreover, the term "stable" especially means that the composition according to the invention should not undergo any sedimentation of the particles present, for example of the pigments and/or nacres, when the composition comprises such compounds, especially after 72 hours or even 1 month at 42° C.

Preferably, no sedimentation of the pigments and/or nacres should be observed in a composition comprising a total pigment and/or nacre content of greater than or equal to 1% by weight and preferably greater than or equal to 2% by weight, relative to the weight of the composition, after 72 hours at 25° C. or at 42° C., and preferably nor after 1 month at 42° C.

Moreover, the term "stable" also preferably means that no sedimentation of the pigments and/or nacres should be observed after the composition according to the invention has been subjected to a centrifugation at 450 rpm for 10 minutes.

In particular, the composition according to the invention is easy to apply to the skin and/or the lips. The ease of application is especially reflected in terms of the glidance and/or the ease of spreading.

The composition may be in solid or liquid form.

Preferably, the composition is in liquid form at room temperature (20-25° C.). For the purposes of the present invention, the terms "liquid" and "fluid" characterize the state of a composition at room temperature (between 20 and 25° C.) and at atmospheric pressure (760 mmHg). The term "liquid" especially means a fluid composition, as opposed to a solid composition.

Particularly preferably, the composition according to the invention is a makeup composition, preferably for the lips, such as a lip gloss or a solid lipstick, which may, for example, be in the form of a wand.

According to another aspect, the present invention relates to a cosmetic process for making up and/or caring for the lips, comprising the application to the lips and/or the skin of a cosmetic composition as defined previously. Particularly preferably, the invention relates to a process preferably for making up the lips, comprising the application to the lips of a cosmetic composition as defined previously.

In that which follows, the expression "at least one" is equivalent to "one or more" and, unless otherwise indicated, the limits of a range of values are included within this range.

Physiologically Acceptable Medium

The term "physiologically acceptable medium" is intended to denote a medium that is particularly suitable for the application of a composition of the invention to the skin or the lips.

The physiologically acceptable medium is generally adapted to the nature of the support onto which the composition has to be applied, and also to the appearance under which the composition has to be packaged.

The composition according to the invention comprises less than 5% by weight of water relative to the total weight of the composition.

Preferably, the composition according to the invention comprises less than 2% by weight of water relative to the total weight of the composition.

Particularly preferably, the composition according to the invention is anhydrous. The term "anhydrous" especially means that water is preferably not deliberately added to the compositions, but may be present in trace amounts in the various compounds used in the compositions.

Hydrophobic Silica Aerogels

The composition according to the invention comprises at least silica aerogel particles.

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying operations are described in detail in Brinker C. J. and Scherer G. W., Sol-Gel Science, New York, Academic Press, 1990.

The hydrophobic silica aerogel particles used in the present invention exhibit a specific surface area per unit of mass ($S_M$) ranging from 500 to 1500 $m^2/g$, preferably from 600 to 1200 $m^2/g$ and better still from 600 to 800 $m^2/g$, and a size, expressed as the volume-mean diameter (D[0.5]), ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to one embodiment, the hydrophobic silica aerogel particles used in the present invention have a size, expressed as the volume-mean diameter (D[0.5]), ranging from 1 to 30 μm, preferably from 5 to 25 μm, better still from 5 to 20 μm and even better still from 5 to 15 μm.

The specific surface area per unit of mass can be determined by the nitrogen absorption method, known as the BET (Brunauer-Emmett-Teller) method, described in The Journal of the American Chemical Society, Vol. 60, page 309, February 1938 and corresponding to the international standard ISO 5794/1 (appendix D). The BET specific surface area corresponds to the total specific surface area of the particles under consideration.

The sizes of the silica aerogel particles can be measured by static light scattering using a commercial particle size analyser of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

According to one advantageous embodiment, the hydrophobic silica aerogel particles used in the present invention have a specific surface area per unit of mass ($S_M$) ranging from 600 to 800 $m^2/g$ and a size expressed as the volume-mean diameter (D[0.5]) ranging from 5 to 20 μm and even better still from 5 to 15 μm.

The silica aerogel particles used in the present invention may advantageously have a tapped density ρ ranging from 0.02 $g/cm^3$ to 0.10 $g/cm^3$, preferably from 0.03 $g/cm^3$ to 0.08 $g/cm^3$ and preferably from 0.05 $g/cm^3$ to 0.08 $g/cm^3$.

In the context of the present invention, this density, ρ known as the tapped density, may be assessed according to the following protocol:

40 g of powder are poured into a measuring cylinder; the measuring cylinder is then placed on a Stay 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tapped density is determined by the ratio w/Vf, in this instance 40/Vf (Vf being expressed in $cm^3$ and w in g).

According to one preferred embodiment, the hydrophobic silica aerogel particles used in the present invention have a specific surface area per unit of volume $S_V$ ranging from 5 to 60 $m^2/cm^3$, preferably from 10 to 50 $m^2/cm^3$ and better still from 15 to 40 $m^2/cm^3$.

The specific surface area per unit of volume is given by the relationship: $S_V = S_M \times \rho$, where ρ is the tapped density, expressed in $g/cm^3$, and $S_M$ is the specific surface area per unit of weight, expressed in $m^2/g$, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or method of determination of oil uptake of a powder described in the standard NF T 30-022. It corresponds to the amount of oil adsorbed onto the available surface of the powder and/or absorbed by the powder by measurement of the wet point, described below:

An amount m=2 g of powder is placed on a glass plate and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added at the rate of one drop at a time and the mixture is subsequently triturated with the spatula. The addition of oil is stopped when a firm and smooth paste is obtained. This paste must be able to be spread over the glass plate without cracks or the formation of lumps.

The volume Vs (expressed in ml) of oil used is then noted.

The oil uptake corresponds to the ratio Vs/m.

The aerogels used according to the present invention are hydrophobic silica aerogels, preferably of silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles modified at the surface by silylation, reference may be made to the document U.S. Pat. No. 7,470,725.

Use will preferably be made of hydrophobic silica aerogel particles surface-modified with trimethylsilyl groups.

Mention may be made, as hydrophobic silica aerogels which can be used in the invention, for example, of the aerogel sold under the name VM-2260 (INCI name: Silica silylate) by Dow Corning, the particles of which have a mean size of approximately 1000 microns and a specific surface area per unit of mass ranging from 600 to 800 $m^2/g$.

Mention may also be made of the aerogels sold by Cabot under the references Aerogel TLD 201, Aerogel OGD 201, Aerogel TLD 203, Enova® Aerogel MT 1100 and Enova Aerogel MT 1200.

Use will be made more particularly of the aerogel sold under the name VM-2270 (INCI name: Silica silylate), by the company Dow Corning, the particles of which have an average size ranging from 5-15 microns and a specific surface area per unit of mass ranging from 600 to 800 m2/g.

Preferably, the hydrophobic silica aerogel particles are present in the composition according to the invention in an active material content ranging from 0.1% to 15% by weight and preferably from 0.1% to 10% by weight relative to the total weight of the composition.

Preferably, the hydrophobic silica aerogel particles are present in the composition according to the invention in an active material content ranging from 0.1% to 6% by weight and more preferably from 0.2% to 4% by weight relative to the total weight of the composition.

The hydrophobic silica aerogel particles may be used, especially in the context of the composition according to the invention, in a content range less than that conventionally used for the fillers conventionally used, especially in lip gloss compositions, such as nanosilica particles, such as the compound whose INCI name is Silica Dimethyl Silylate, sold especially under the reference Aerosil® R 972 by Evonik Degussa. Specifically, nanosilica particles are conventionally used in a weight content of between 2% and 7% by weight relative to the total weight of the composition.

This may prove to be advantageous in particular in the case of compositions for which it is important to be able to obtain a glossy deposit, in particular in the case of lip compositions, such as lip glosses (or sticks for solid compositions). Specifically, since fillers have a matting effect on the deposits obtained with the compositions, it is advantageous to be able to thicken and/or gel the formula sufficiently without thereby affecting the glossy nature of the deposit obtained, or doing so as little as possible.

Wax

The composition according to the invention preferably comprises at least one wax. Preferably, the wax is a wax with a melting point of greater than or equal to 60° C. and preferably greater than or equal to 65° C.

According to a preferred embodiment, the composition according to the invention comprises a total content of wax(es) ranging from 0.1% to 15% by weight and better still from 0.5% to 10% by weight relative to the total weight of the composition.

According to a preferred embodiment, the composition according to the invention comprises a total content of wax(es) ranging from 1% to 10% by weight and better still from 1% to 7% by weight relative to the total weight of the composition.

According to a preferred embodiment, the composition according to the invention comprises a total content of wax(es) with a melting point of greater than or equal to 60° C. and preferably greater than or equal to 65° C. ranging from 0.1% to 15% by weight and better still from 0.5% to 10% by weight relative to the total weight of the composition.

According to a preferred embodiment, the composition according to the invention comprises a total content of wax(es) with a melting point of greater than or equal to 60°

C. and preferably greater than or equal to 65° C. ranging from 1% to 10% by weight and better still from 1% to 7% by weight relative to the total weight of the composition.

The term "wax" under consideration in the context of the present invention generally means a lipophilic compound that is solid at room temperature (25° C.), with a reversible solid/liquid change of state, having a melting point of greater than or equal to 30° C., which may be up to 200° C. and in particular up to 120° C.

For the purposes of the invention, the melting point corresponds to the temperature of the most endothermic peak observed on thermal analysis (DSC) as described in standard ISO 11357-3; 1999. The melting point of the wax can be measured using a differential scanning calorimeter (DSC), for example the calorimeter sold under the name MDSC 2920 by TA Instruments.

The measurement protocol is as follows:

A sample of 5 mg of wax placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature increase ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the value of the temperature corresponding to the tip of the peak of the curve representing the variation in the difference in power absorbed as a function of the temperature.

The waxes that may be used in the compositions according to the invention are chosen from waxes that are solid at room temperature of animal, vegetable, mineral or synthetic origin, and mixtures thereof.

As illustrations of waxes with a melting point of greater than or equal to 60° C., mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, microcrystalline waxes, ozokerite, polyethylene waxes, 12-hydroxystearic acid, glyceryl trihydroxystearate, the waxes obtained by Fischer-Tropsch synthesis and waxy copolymers, and also esters thereof, and mixtures thereof.

Mention may also be made of waxes obtained by catalytic hydrogenation of animal or plant oils containing linear or branched $C_8$-$C_{32}$ fatty chains. Among these waxes that may especially be mentioned are isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-45® by the company Heterene.

Mention may also be made of silicone waxes ($C_{30-45}$ alkyl dimethicone) and fluoro waxes.

The waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

A wax that may be used is a $C_{20}$-$C_{40}$ alkyl (hydroxystearyloxy)stearate (the alkyl group containing from 20 to 40 carbon atoms), alone or as a mixture.

Such a wax is especially sold under the names Kester Wax K 82 P®, Hydroxypolyester K 82 P® and Kester Wax K 80 P® by the company Koster Keunen.

A wax that may also be used is a linear hydroxylated C18-C24 fatty acid, for instance the 12-hydroxystearic acid sold especially under the reference 12-Hydroxystearic Acid Premium Grade 12H-P by the company That Kawaken.

Preferably, the said wax(es) with a melting point of greater than or equal to 60° C. are chosen from carnauba wax, ozokerite, microcrystalline wax, 12-hydroxystearic acid, a polyethylene wax (for example those sold under the names Performalene 500 L Polyethylene or Performalene 400 L Polyethylene by New Phase Technologies, or Asensa SC 211 from Honeywell), polymethylene waxes (for example the product sold under the reference Cirebelle 108 by Cirebelle), beeswax, candelilla wax, hydroxyoctacosanyl hydroxystearate, hydrogenated castor oil, hydrogenated jojoba oil, rice bran wax, polyglycerolated beeswax, octacosanyl stearate, ceresin wax, $C_{20}$-$C_{40}$ alkyl (hydroxystearyloxy)stearate waxes, 12-hydroxystearic acid, polyethylene alcohol wax, Fischer-Tropsch wax, the waxes obtained by hydrogenation of castor oil esterified with cetyl alcohol, ouricury wax, montan wax, the glyceryl trihydroxystearate whose INCI name is Trihydroxystearin (sold, for example, by Elementis under the name Thixcin R), and mixtures thereof.

Preferably, the wax with a melting point of greater than or equal to 60° C. is chosen from carnauba wax, ozokerite, microcrystalline wax, polyethylene wax, beeswax, candelilla wax, hydrogenated jojoba oil, 12-hydroxystearic acid and glyceryl trihydroxystearate, and mixtures thereof.

Preferably, the composition according to the invention comprises at least one wax with a melting point of greater than or equal to 65° C., preferably chosen from carnauba wax, ozokerite, microcrystalline wax, 12-hydroxystearic acid, a polyethylene wax (for example those sold under the names Performalene 500 L Polyethylene or Performalene 400 L Polyethylene by New Phase Technologies), candelilla wax, hydroxyoctacosanyl hydroxystearate, hydrogenated castor oil, hydrogenated jojoba oil, rice bran wax, polyglycerolated beeswax, octacosanyl stearate, ceresin wax, $C_{20}$-$C_{40}$ alkyl (hydroxystearyloxy)stearate waxes, polyethylene alcohol wax, Fischer-Tropsch wax, the waxes obtained by hydrogenation of castor oil esterified with cetyl alcohol, ouricury wax, montan wax, the glyceryl trihydroxystearate whose INCI name is Trihydroxystearin (sold, for example, by Elementis under the name Thixcin R), and mixtures thereof.

Preferably, the composition according to the invention comprises at least one wax with a melting point of greater than or equal to 65° C. chosen from carnauba wax, ozokerite, microcrystalline wax, polyethylene wax, 12-hydroxystearic acid, candelilla wax, hydrogenated jojoba oil and glyceryl trihydroxystearate, and mixtures thereof.

Wax with a Melting Point of Less than 60° C.

The composition according to the invention may also comprise at least one wax with a melting point of less than 60° C. Such a wax may be chosen in particular from paraffin wax, stearyl alcohol, hydrogenated cocoglycerides, synthetic beeswax (especially the product sold under the reference Cyclochem 326 A by Evonik Goldschmidt), palm butter, sumach wax, silicone beeswax, stearyl stearate, alkyl dimethicone wax, certain polymethylene waxes (such as Cirebelle 303 sold by Cirebelle), berry wax, olive wax and lemon wax, and mixtures thereof.

In particular, according to a first embodiment, the composition according to the invention may comprise a content of wax(es) with a melting point of less than 60° C. ranging from 0.1% to 10% by weight and better still from 0.5% to 5% by weight relative to the total weight of the composition.

In particular, according to a second embodiment, the composition according to the invention may be free of wax(es) with a melting point of less than 60° C.

Liquid Fatty Phase

The composition according to the invention comprises at least one oil, in particular preferably at least one non-volatile oil.

The term "oil" means a water-immiscible non-aqueous compound that is liquid at room temperature (25° C.) and at atmospheric pressure (760 mmHg).

In particular, the oil (preferably a non-volatile oil) may be chosen from hydrocarbon-based oils, silicone oils and/or fluoro oils, and mixtures thereof.

Preferentially, the oil may be chosen from hydrocarbon-based oils and/or silicone oils.

Non-Volatile Oils

Preferably, the composition according to the invention comprises at least one non-volatile oil.

The term "non-volatile" oil refers to an oil for which the vapour pressure at room temperature and atmospheric pressure is non-zero and less than 0.02 mmHg (2.66 Pa) and better still less than $10^{-3}$ mmHg (0.13 Pa).

The non-volatile oils may be hydrocarbon oils especially of vegetable origin, oils of synthetic or mineral origin, silicone oils, fluoro oils, or mixtures thereof.

Apolar Oils

According to a first embodiment, the said non-volatile oil may be an apolar oil, preferably an apolar hydrocarbon-based oil.

These oils may be of vegetable, mineral or synthetic origin.

For the purposes of the present invention, the term "apolar oil" means an oil whose solubility parameter at 25° C., $\delta_a$, is equal to 0 $(J/cm^3)^{1/2}$.

The definition and calculation of the solubility parameters in the Hansen three-dimensional solubility space are described in the paper by C. M. Hansen: "The three-dimensional solubility parameters", J. Paint Technol., 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

The term "hydrocarbon-based oil" means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

Preferably, the non-volatile apolar hydrocarbon-based oil may be chosen from linear or branched hydrocarbons of mineral or synthetic origin, such as:

liquid paraffin or derivatives thereof, squalane, isoeicosane, naphthalene oil, polybutylenes such as Indopol H-100 (molar mass or MW=965 g/mol), Indopol H-300 (MW=1340 g/mol) and Indopol H-1500 (MW=2160 g/mol) sold or manufactured by the company Amoco, polyisobutenes, hydrogenated polyisobutylenes such as Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), or alternatively Parleam Lite sold by NOF Corporation, decene/butene copolymers, polybutene/polyisobutene copolymers, especially Indopol L-14, polydecenes and hydrogenated polydecenes such as: Puresyn 10 (MW=723 g/mol) and Puresyn 150 (MW=9200 g/mol) sold or manufactured by the company Mobil Chemicals, or alternatively Puresyn 6 sold by ExxonMobil Chemical), and their mixtures.

Preferably, the composition according to the invention comprises at least one apolar oil preferably chosen from polybutenes, polyisobutenes, hydrogenated polyisobutenes, polydecenes and/or hydrogenated polydecenes, and mixtures thereof.

A composition according to the invention may comprise a content of apolar oil(s), which is preferably non-volatile, ranging from 5% to 60%, for example from 10% to 45% by weight and preferably from 15% to 40% by weight, relative to the total weight of the composition.

According to one preferred embodiment, a composition in accordance with the invention comprises at least one apolar hydrocarbon-based oil preferably chosen from hydrogenated polyisobutylene and hydrogenated polydecene.

Polar Oils

According to a particular embodiment, the composition comprises at least one non-volatile polar oil. The said oil may be a hydrocarbon-based oil, silicone oil or fluoro oil.

Preferentially, the said non-volatile oil is a polar hydrocarbon-based oil.

The term "silicone oil" means an oil containing at least one silicon atom, and especially containing Si—O groups.

The term "fluoro oil" means an oil containing at least one fluorine atom.

These oils may be of vegetable, mineral or synthetic origin.

The term "hydrocarbon-based oil" means an oil formed essentially from, or even constituted by, carbon and hydrogen atoms, and possibly oxygen and nitrogen atoms, and not containing any silicon or fluorine atoms. It may contain alcohol, ester, ether, carboxylic acid, amine and/or amide groups.

Within the meaning of the present invention, the term "polar oil" means an oil for which the solubility parameter at 25° C., $\delta_a$, is other than 0 $(J/cm^3)^{1/2}$.

In particular, the hydrocarbon-based non-volatile polar oil may be chosen from the list of oils below, and mixtures thereof:

hydrocarbon vegetable oils such as liquid triglycerides of fatty acids containing from 4 to 10 carbon atoms, for instance heptanoic or octanoic acid triglycerides or jojoba oil;

ester oils, preferably chosen from:

fatty acid esters, in particular of 4 to 22 carbon atoms, and especially of octanoic acid, heptanoic acid, lanolic acid, oleic acid, lauric acid or stearic acid, for instance propylene glycol dioctanoate, propylene glycol monoisostearate or neopentyl glycol diheptanoate;

synthetic esters, for instance the oils of formula $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms, on condition that $R_1+R_2 \geq 16$, for instance purcellin oil (cetostearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or 2-diethylhexyl succinate; preferably, the preferred synthetic esters $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms are such that $R_1$ and $R_2 \geq 20$;

linear fatty acid esters with a total carbon number ranging from 35 to 70, for instance pentaerythrityl tetrapelargonate (MW=697 g/mol);

glyceryl esters such as the caprylic/capric glyceride sold under the reference Capmul MCM by the company Abitec;

hydroxylated esters, preferably with a total carbon number ranging from 35 to 70, for instance polyglyceryl-2 triisostearate (MW=965 g/mol), isostearyl lactate, octyl hydroxystearate, octyldodecyl hydroxystearate, diisostearyl malate, glyceryl stearate; diethylene glycol diisononanoate;

esters of aromatic acids and of alcohols comprising 4 to 22 atoms, such as tridecyl trimellitate (MW=757 g/mol);

$C_{24}$-$C_{28}$ esters of branched fatty alcohols or fatty acids such as those described in patent application EP-A-0 955 039, and especially triisoarachidyl citrate (MW=1033.76 g/mol), pentaerythrityl tetraisononanoate (MW=697 g/mol), glyceryl triisostearate (MM=891 g/mol), glyceryl tris(2-decyl)tetradecanoate (MW=1143 g/mol), pentaerythrityl tetraisostearate (MW=1202 g/mol), polyglyceryl-2 tetraisostearate (MW=1232 g/mol) or pentaerythrityl tetrakis(2-decyl)tetradecanoate (MW=1538 g/mol), polyesters resulting from the esterification of at least one hydroxylated carboxylic acid triglyceride with an aliphatic monocarboxylic acid and with an aliphatic dicarboxylic acid, which is optionally unsaturated, for instance the succinic acid and isostearic acid castor oil sold under the reference Zenigloss by Zenitech;

esters of a diol dimer and of a diacid dimer of general formula HO—$R^1$—(—OCO—$R^2$—COO—$R^1$—)$_h$—OH, in which:

$R^1$ represents a diol dimer residue obtained by hydrogenation of dilinoleic diacid, $R^2$ represents a hydrogenated dilinoleic diacid residue, and h represents an integer ranging from 1 to 9, especially the esters of dilinoleic diacids and of dilinoleyl diol dimers sold by the company Nippon Fine Chemical under the trade names Lusplan DD-DA5® and DD-DA7®, polyesters obtained by condensation of an unsaturated fatty acid dimer and/or trimer and of diol, such as those described in patent application FR 0 853 634, in particular such as dilinoleic acid and 1,4-butanediol. Mention may especially be made in this respect of the polymer sold by Biosynthis under the name Viscoplast 14436H (INCI name: dilinoleic acid/butanediol copolymer), or copolymers of polyols and of diacid dimers, and esters thereof, such as Hailuscent ISDA;

fatty alcohols containing from 12 to 26 carbon atoms, which are preferably branched, for instance octyldodecanol, 2-butyloctanol, 2-hexyldecanol, 2-undecylpentadecanol and oleyl alcohol;

$C_{12}$-$C_{22}$ higher fatty acids, such as oleic acid, linoleic acid and linolenic acid, and mixtures thereof;

oils of plant origin such as sesame oil (820.6 g/mol); and the C18-36 acid triglyceride (Dub TGI 24 from Stéarineries Dubois);

fatty acids containing from 12 to 26 carbon atoms, for instance oleic acid;

dialkyl carbonates, the two alkyl chains possibly being identical or different, such as dicaprylyl carbonate sold under the name Cetiol CC® by Cognis; and vinylpyrrolidone copolymers such as the vinylpyrrolidone/1-hexadecene copolymer, Antaron V-216 sold or manufactured by the company ISP (MW=7300 g/mol).

According to one particular embodiment, a composition in accordance with the invention comprises at least one vinylpyrrolidone/1-hexadecene copolymer and/or at least isopropyl myristate.

Preferably, the polar non-volatile hydrocarbon-based oil is chosen from hydrocarbon-based oils from plants or of plant origin, ester oils, fatty alcohols containing from 12 to 26 carbon atoms, fatty acids containing from 12 to 26 carbon atoms and vinylpyrrolidone copolymers, and mixtures thereof.

Preferably, the composition according to the invention comprises at least one non-volatile oil chosen from synthetic esters of formula $R_1COOR_2$ in which $R_1$ represents a linear or branched fatty acid residue containing from 4 to 40 carbon atoms and $R_2$ represents a hydrocarbon-based chain that is especially branched, containing from 4 to 40 carbon atoms, provided that $R_1+R_2 \geq 16$.

Preferably, the composition according to the invention comprises at least one non-volatile ester oil chosen from purcellin oil (cetostearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate and 2-diethylhexyl succinate.

Preferably, the composition according to the invention comprises at least one non-volatile oil chosen from neopentanoic acid esters, preferably octyldodecyl neopentanoate.

Preferably, the composition comprises a content of non-volatile ester oil ranging from 5% to 40% by weight and preferably from 10% to 30% by weight relative to the total weight of the composition.

According to another embodiment, the polar non-volatile oil may be a fluoro oil.

The term "fluoro oil" means an oil comprising at least one fluorine atom.

The fluoro oils that may be used according to the invention may be chosen from fluorosilicone oils, fluoro polyethers and fluorosilicones as described in document EP-A-847 752, and perfluoro compounds.

According to the invention, the term "perfluoro compounds" means compounds in which all the hydrogen atoms have been replaced with fluorine atoms.

According to one preferred embodiment, the fluoro oil according to the invention is chosen from perfluoro oils.

As examples of perfluoro oils that may be used in the invention, mention may be made of perfluorodecalins and perfluoroperhydrophenanthrenes.

According to one preferred embodiment, the fluoro oil is chosen from perfluoroperhydrophenanthrenes, and especially the Fiflow® products sold by the company Creations Couleurs. In particular, use may be made of the fluoro oil for which the INCI name is Perfluoroperhydrophenanthrene, sold under the reference Fiflow 220 by the company F2 Chemicals.

According to another embodiment, the polar non-volatile oil may be a silicone oil.

The non-volatile silicone oil that may be used in the invention may be chosen especially from silicone oils especially with a viscosity at 25° C. of greater than or equal to 9 centistokes (cSt) ($9 \times 10^{-6}$ m$^2$/s) and less than 800 000 cSt, preferably between 50 and 600 000 cSt and preferably between 100 and 500 000 cSt. The viscosity of this silicone may be measured according to standard ASTM D-445.

In particular, the non-volatile silicone oil may be chosen from:
  linear or branched non-volatile polydimethylsiloxanes (PDMS);
  polydimethylsiloxanes comprising alkyl, alkoxy or phenyl groups, which are pendent or at the end of the silicone chain, these groups containing from 2 to 24 carbon atoms, for instance the cetyl dimethicone sold under the reference Abil Wax 9801 by Evonik Goldschmidt;
  phenyl silicone oils, in particular chosen from:
  phenyl trimethicones, especially such as phenyl trimethylsiloxy trisiloxane, sold especially under the reference Dow Corning 556 Cosmetic Grade Fluid;
  phenyl dimethicones;
  phenyl trimethylsiloxy diphenylsiloxanes;
  diphenyl dimethicones;
  diphenyl methyldiphenyl trisiloxanes;
  2-phenylethyl trimethylsiloxysilicates; and
  trimethyl pentaphenyl trisiloxane, especially such as the silicone oil sold by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane); and
  trimethyl siloxyphenyl dimethicones, especially such as the product sold under the reference Belsil PDM 1000 by the company Wacker.

Preferably, the said non-volatile oil present in the composition is chosen from:
  hydrocarbon-based oils, preferably chosen from apolar hydrocarbon-based oils such as polybutenes, polyisobutenes, hydrogenated polyisobutenes, polydecenes and/or hydrogenated polydecenes, and mixtures thereof, and polar hydrocarbon-based oils, preferably chosen from hydrocarbon-based oils from plants or of plant origin, ester oils, fatty alcohols containing from 12 to 26 carbon atoms, fatty acids containing from 12 to 26 carbon atoms and vinylpyrrolidone copolymers, and mixtures thereof,
  silicone oils, preferably chosen from linear or branched, non-volatile polydimethylsiloxanes and/or polydimethylsiloxanes comprising alkyl, alkoxy or phenyl groups, which are pendent or at the end of the silicone chain, these groups containing from 2 to 24 carbon atoms, for instance cetyl dimethicone and/or phenyl silicone oils, which are preferably non-volatile; fluoro oils,
  and mixtures thereof.

A composition according to the invention may comprise a total content of non-volatile polar oil, which is preferably hydrocarbon-based, ranging from 5% to 60% by weight, for example from 10% to 45% by weight and preferably from 15% to 40% by weight relative to the total weight of the composition.

According to one preferred embodiment, the non-volatile oil(s), which are preferably hydrocarbon-based, are present in a total content ranging from 15% to 90% by weight, in particular from 25% to 80% by weight and preferably from 35% to 70% by weight relative to the total weight of the composition.

Non-Volatile Oil with a Molecular Mass of Greater than 400 g/mol

According to a preferred embodiment, the composition according to the invention comprises at least one non-volatile oil with a molecular mass of greater than 400 g/mol, preferably as defined above.

Preferably, the composition according to the invention may comprise a total content of oil(s) with a molecular mass of greater than 400 g/mol ranging from 5% to 80% by weight, for example from 5% to 60% by weight and preferably from 5% to 50% by weight relative to the total weight of the core composition.

More precisely, such an oil may be a hydrocarbon-based or silicone oil with a molecular mass of greater than 400 g/mol, or even 500 g/mol, especially 650 g/mol. In particular, this glossy oil may have a molar mass ranging from 400 to 10 000 g/mol and in particular from 650 to 10 000 g/mol.

Preferably, the composition according to the invention comprises at least one hydrocarbon-based or silicone oil with a molecular mass ranging from 650 to 5000 g/mol.

This oil with a molecular mass of greater than 400 g/mol may be polar or apolar. This oil with a molecular mass of greater than 400 g/mol is advantageously an oil chosen from oils of high molar mass, in particular having a molar mass ranging from 500 to 10 000 g/mol, in particular from 500 to 8000 g/mol and more particularly from 550 to 7500 g/mol.

Preferably, the oil with a molecular mass of greater than 400 g/mol has a refractive index of greater than or equal to 1.45, especially ranging from 1.45 to 1.6.

The oil with a molecular mass of greater than 400 g/mol is preferably a non-volatile oil.

Advantageously, a hydrocarbon-based oil with a molecular mass of greater than 400 g/mol that may be used in the present invention may be chosen from:
  apolar polymeric oils, preferably chosen from:
    polybutylenes, for instance Indopol H-100 (molar mass or MW=965 g/mol), Indopol H-300 (MW=1340 g/mol) and Indopol H-1500 (MW=2160 g/mol) sold or manufactured by the company Amoco, and/or hydrogenated polyisobutylenes, for instance Panalane H300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), and/or polydecenes and hydrogenated polydecenes, for instance: Puresyn 10 (MW=723 g/mol) and Puresyn 150 (MW=9200 g/mol) sold or manufactured by the company Mobil Chemicals, and mixtures thereof, ester oils, preferably chosen from:

linear fatty acid esters with a total carbon number ranging from 35 to 70, for instance pentaerythrityl tetrapelargonate (MW=697 g/mol);

hydroxylated esters such as for example polyglyceryl-2 triisostearate (MW=965 g/mol), triisocetyl citrate (MW=864 g/mol), diisostearyl malate (MW=639 g/mol);

aromatic esters, for instance tridecyl trimellitate such as the product sold by the company Lipo Chemicals under the name Liponate TDTM (MW=757 g/mol), $C_{24}$-$C_{28}$ branched fatty alcohol or fatty acid esters such as those described in patent application EP-A-0 955 039, and especially triisoarachidyl citrate (MW=1033.76 g/mol), pentaerythrityl tetraisononanoate (MW=697 g/mol), glyceryl triisostearate (MM=891 g/mol), glyceryl tris(2-decyl)tetradecanoate (MW=1143 g/mol), pentaerythrityl tetraisostearate (MW=1202 g/mol), polyglyceryl-2 tetraisostearate (MW=1232 g/mol) or pentaerythrityl tetrakis(2-decyl)tetradecanoate (MW=1538 g/mol);

a polyester resulting from the esterification of at least one triglyceride of hydroxylated carboxylic acid(s) with an aliphatic monocarboxylic acid and with an aliphatic dicarboxylic acid, which is optionally unsaturated, for instance the succinic acid and isostearic acid castor oil sold under the reference Zenigloss by Zenitech, esters of a diol dimer and of a diacid dimer of general formula HO—$R^1$—(—OCO—$R^2$—COO—$R^1$—)$_h$—OH, in which $R^1$ represents a diol dimer residue obtained by hydrogenation of dilinoleic diacid, $R^2$ represents a hydrogenated dilinoleic diacid residue and h represents an integer ranging from 1 to 9, especially the dilinoleic diacid esters of dilinoleic diol dimers sold by the company Nippon Fine Chemical under the trade names Lusplan DD-DA5® and DD-DA7®, oils of plant origin, for instance sesame oil (MW=820 g/mol), vinylpyrrolidone copolymers such as the vinylpyrrolidone/1-hexadecene copolymer, Antaron V-216 sold or manufactured by the company ISP (MW=7300 g/mol), and mixtures thereof.

The oil with a molecular mass of greater than 400 g/mol may also be an oil chosen from silicone oils and in particular oils chosen from polydimethylsiloxanes (PDMS); phenyl silicone oils such as phenyl trimethicones (such as the phenyl trimethicone sold under the trade name DC 556 by Dow Corning), phenyl dimethicones, phenyltrimethylsiloxydiphenylsiloxanes, diphenyl dimethicones, diphenylmethyldiphenyltrisiloxane, trimethylpentaphenyltrisiloxane (especially the 1,3,5-trimethyl-1,1,3,5,5-pentaphenyltrisiloxane sold under the name PH-1555 HRI Cosmetic Fluid by Dow Corning), and mixtures thereof.

Non-Volatile Oil with a Molecular Mass of Less than 400 g/mol

The composition according to the invention may comprise at least one non-volatile oil with a molecular mass of less than 400 g/mol. This oil may be a hydrocarbon-based or silicone oil.

Preferably, the non-volatile oil with a molecular mass of less than 400 g/mol is chosen from:

synthetic esters, especially of fatty acids, for instance the oils of formula $R_1COOR_2$ in which $R_1$ represents a linear or branched higher fatty acid residue containing from 1 to 30 carbon atoms and $R_2$ represents a hydrocarbon-based chain, which is especially branched, containing from 1 to 30 carbon atoms, with $13<R_1+R_2<30$, for instance purcellin oil (cetostearyl octanoate), isononyl isononanoate, isopropyl myristate, isopropyl palmitate, $C_{12}$-$C_{15}$ alkyl benzoates, hexyl laurate, diisopropyl adipate, 2-ethylhexyl palmitate, isostearyl isostearate; alcohol or polyalcohol octanoates, decanoates or ricinoleates, for instance propylene glycol dioctanoate; hydroxylated esters, for instance isostearyl lactate or octyl hydroxystearate; polyol esters, for instance propylene glycol dioctanoate, neopentyl glycol diheptanoate or diethylene glycol diisononanoate; and/or fatty alcohols that are liquid at room temperature, with a branched and/or unsaturated carbon-based chain containing from 8 to 26 carbon atoms, such as oleyl alcohol, linoleyl alcohol, linolenyl alcohol, isostearyl alcohol or octyldodecanol, as sold under the trade reference Eutanol G® by the company Cognis; and/or oleic acid or linoleic acid fatty acids, for instance oleic acid, linoleic acid or linolenic acid; and/or silicone oils such as polydimethylsiloxanes (PDMS); and mixtures thereof.

Volatile Oils

According to a first embodiment, the composition according to the invention may comprise a volatile oil.

For the purposes of the invention, the term "volatile oil" means an oil that is capable of evaporating on contact with keratin materials in less than one hour, at room temperature and atmospheric pressure (760 mmHg). The volatile organic solvent(s) and volatile oils of the invention are volatile organic solvents and cosmetic oils that are liquid at room temperature, with a non-zero vapour pressure at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

These oils may be hydrocarbon-based oils, silicone oils or fluoro oils, or mixtures thereof.

In particular, volatile oils that may be mentioned include volatile hydrocarbon-based oils and especially volatile hydrocarbon-based oils with a flash point of less than or equal to 80° C. (the flash point is in particular measured according to ISO Standard 3679), such as hydrocarbon-based oils containing from 8 to 14 carbon atoms, and especially:

branched $C_8$-$C_{14}$ alkanes, for instance $C_8$-$C_{14}$ isoalkanes of petroleum origin (also known as isoparaffins), for instance isododecane (also known as 2,2,4,4,6-pentamethylheptane), isodecane, and, for example, the oils sold under the trade name Isopar or Permethyl, linear alkanes, for example such as n-dodecane (C12) and n-tetradecane (C14) sold by Sasol under the references, respectively, Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, and mixtures thereof.

The volatile solvent is preferably chosen from volatile hydrocarbon-based oils containing from 8 to 14 carbon atoms, and mixtures thereof.

As other volatile hydrocarbon-based oils, and especially as volatile hydrocarbon-based oils with a flash point of less than or equal to 80° C., mention may also be made of ketones that are liquid at room temperature, such as methyl ethyl ketone or acetone; short-chain esters (containing from 3 to 8 carbon atoms in total) such as ethyl acetate, methyl acetate, propyl acetate or n-butyl acetate; ethers that are liquid at room temperature, such as diethyl ether, dimethyl ether or dichlorodiethyl ether; alcohols and especially linear or branched lower monoalcohols containing from 2 to 5 carbon atoms, such as ethanol, isopropanol or n-propanol.

A volatile hydrocarbon-based oil with a flash point of greater than 80° C. that may be mentioned is isohexadecane.

According to a second embodiment, the composition according to the invention is free of volatile oil.

Pasty Fatty Substances

According to a particularly preferred embodiment, the composition according to the invention comprises at least one pasty fatty substance.

For the purposes of the present invention, the term "pasty fatty substance" is intended to denote a lipophilic fatty compound that undergoes a reversible solid/liquid change of state, exhibiting anisotropic crystal organization in the solid state, and that comprises, at a temperature of 23° C., a liquid fraction and a solid fraction.

In other words, the starting melting point of the pasty fatty substance can be less than 23° C. The liquid fraction of the pasty fatty substance, measured at 23° C., can represent from 9% to 97% by weight of the pasty fatty substance. This liquid fraction at 23° C. preferably represents between 15% and 85% and more preferably between 40% and 85% by weight.

For the purposes of the invention, the melting point corresponds to the temperature of the most endothermic peak observed in thermal analysis (DSC) as described in the standard ISO 11357-3; 1999. The melting point of a pasty fatty substance can be measured using a differential scanning calorimeter (DSC), for example the calorimeter sold under the name MDSC 2920 by TA Instruments.

The measurement protocol is as follows:

A sample of 5 mg of pasty fatty substance placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of pasty fatty substance is measured as a function of the temperature. The melting point of the pasty fatty substance is the value of the temperature corresponding to the top of the peak of the curve representing the variation in the difference in power absorbed as a function of the temperature.

The liquid fraction by weight of the pasty fatty substance at 23° C. is equal to the ratio of the heat of fusion consumed at 23° C. to the heat of fusion of the pasty fatty substance.

The heat of fusion of the pasty fatty substance is the heat consumed by the latter in order to pass from the solid state to the liquid state. The pasty fatty substance is said to be in the solid state when all of its mass is in crystalline solid form. The pasty fatty substance is said to be in the liquid state when all of its mass is in liquid form.

The enthalpy of fusion of the pasty fatty substance is equal to the area under the curve of the thermogram obtained using a differential scanning calorimeter (DSC), such as the calorimeter sold under the name MDSC 2920 by the company TA Instrument, with a temperature rise of 5° C. or 10° C. per minute, according to Standard ISO 11357-3; 1999.

The heat of fusion of the pasty fatty substance is the amount of energy required to make the pasty fatty substance change from the solid state to the liquid state. It is expressed in J/g.

The heat of fusion consumed at 23° C. is the amount of energy absorbed by the sample to change from the solid state to the state which it exhibits at 23° C., consisting of a liquid fraction and a solid fraction.

The liquid fraction of the pasty fatty substance measured at 32° C. preferably represents from 30% to 100% by weight of the pasty fatty substance, preferably from 50% to 100%, more preferably from 60% to 100% by weight of the pasty fatty substance. When the liquid fraction of the pasty fatty substance measured at 32° C. is equal to 100%, the temperature of the end of the melting range of the pasty fatty substance is less than or equal to 32° C.

The liquid fraction of the pasty fatty substance measured at 32° C. is equal to the ratio of the heat of fusion consumed at 32° C. to the heat of fusion of the pasty fatty substance. The heat of fusion consumed at 32° C. is calculated in the same way as the heat of fusion consumed at 23° C.

The pasty fatty substance may in particular be chosen from synthetic fatty substances and fatty substances of vegetable origin. A pasty fatty substance may be obtained by synthesis from starting materials of plant origin.

The pasty fatty substance may be chosen from:
lanolin and its derivatives,
petroleum jelly (also known as petrolatum),
polyol ethers chosen from polyalkylene glycol pentaerythrityl ethers, fatty alcohol ethers of sugars, and mixtures thereof, the polyethylene glycol pentaerythrityl ether comprising five oxyethylene (5 OE) units (CTFA name: PEG-5 Pentaerythrityl Ether), the polypropylene glycol pentaerythrityl ether comprising 5 oxypropylene (5 OP) units (CTFA name: PPG-5 Pentaerythrityl Ether), and mixtures thereof, and more especially the PEG-5 Pentaerythrityl Ether, PPG-5 Pentaerythrityl Ether and soybean oil mixture, sold under the name Lanolide by Vevy, in which mixture the constituents are in a 46/46/8 ratio by weight: 46% PEG-5 Pentaerythrityl Ether, 46% PPG-5 Pentaerythrityl Ether and 8% soybean oil,
polymeric or nonpolymeric silicone compounds,
polymeric or nonpolymeric fluorinated compounds,
vinyl polymers, in particular:
 olefin homopolymers and copolymers,
 hydrogenated diene homopolymers and copolymers,
 linear or branched oligomers, which are homopolymers or copolymers of alkyl (meth)acrylates preferably containing a $C_8$-$C_{30}$ alkyl group,
 oligomers, which are homopolymers and copolymers of vinyl esters containing $C_8$-$C_{30}$ alkyl groups, and oligomers, which are homopolymers and copolymers of vinyl ethers containing $C_8$-$C_{30}$ alkyl groups, fat-soluble polyethers resulting from the polyetherification between one or more $C_2$-$C_{100}$ and preferably $C_{20}$-$C_{50}$ diols, esters, and/or mixtures thereof.

Among the fat-soluble polyethers that are particularly considered are copolymers of ethylene oxide and/or of propylene oxide with long-chain $C_6$-$C_{30}$ alkylene oxides, more preferably such that the weight ratio of the ethylene oxide and/or propylene oxide to alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Among the esters, the following are especially considered:

esters of an oligomeric glycerol, especially diglycerol esters, in particular condensates of adipic acid and of glycerol, for which some of the hydroxyl groups of the glycerols have reacted with a mixture of fatty acids such as stearic acid, capric acid and isostearic acid, and 12-hydroxystearic acid, for instance bis(diglyceryl) poly(2-acyladipate) sold under the reference Softisan® 649 by the company Sasol, vinyl ester homopolymers containing $C_8$-$C_{30}$ alkyl groups, such as polyvinyl laurate (sold especially under the reference Mexomer PP by the company Chimex), arachidyl propionate, sold under the brand name Waxenol 801 by Alzo, phytosterol esters, fatty acid triglycerides and their derivatives, pentaerythritol esters, esters of a diol dimer and of a diacid dimer, where appropriate esterified on their free alcohol or acid functional group(s) with acid or alcohol radicals, especially dimer dilinoleate esters; such esters may be chosen especially from the esters having the following INCI nomenclature: Bis-Behenyl/Isostearyl/Phytosteryl Dimer Dilinoleyl Dimer Dilinoleate (Plandool G), Phytosteryl/Isostearyl/Cetyl/Stearyl/Behenyl Dimer Dilinoleate (Plandool H or Plandool S), and mixtures thereof, mango butter, such as the product sold under the reference Lipex 203 by the company AarhusKarlshamn, hydrogenated soybean oil, hydrogenated coconut oil, hydrogenated rapeseed oil or mixtures of hydrogenated vegetable oils, such as the soybean, coconut, palm and rapeseed hydrogenated vegetable oil mixture, for example the mixture sold under the reference Akogel® by AarhusKarlshamn (INCI name: Hydrogenated Vegetable Oil), shea butter, in particular that having the INCI name Butyrospermum Parkii Butter, such as that sold under the reference Sheasoft® by AarhusKarlshamn, and mixtures thereof.

According to a preferred embodiment, the pasty fatty substance is chosen from esters and in particular diglycerol esters, and their mixtures.

Among the pasty compounds, bis-behenyl/isostearyl/phytosteryl dimer dilinoleyl, bis(diglyceryl) poly(2-acyladipate), hydrogenated castor oil dimer dilinoleate, for example Risocast DA-L sold by Kokyu Alcohol Kogyo, and hydrogenated castor oil isostearate, for example Salacos HCIS (V-L) sold by Nisshin Oil, polyvinyl laurate, mango butter, shea butter, hydrogenated soybean oil, hydrogenated coconut oil, hydrogenated rape seed oil and vinylpyrrolidone/eicosene copolymers, or a mixture thereof, will preferably be chosen.

According to a particularly preferred embodiment, the composition according to the invention comprises a mixture of pasty fatty substances (i.e. at least two different pasty fatty substances).

According to a particularly preferred embodiment, the composition according to the invention comprises hydrogenated castor oil isostearate, for example Salacos HCIS (V-L) sold by Nisshin Oil. Preferably, according to this embodiment, the composition according to the invention also comprises at least a second pasty fatty substance, other than hydrogenated castor oil isostearate.

Preferably, the composition according to the invention comprises a total content of pasty fatty substance ranging from 0.1% to 50% by weight, especially ranging from 1% to 45% by weight and in particular ranging from 5% to 40% by weight relative to the total weight of the composition.

According to another embodiment, the composition is devoid of pasty fatty substances.

Dextrin Ester

The composition according to the invention may moreover comprise at least one preferably $C_{12}$ to $C_{24}$ and in particular $C_{14}$-$C_{18}$ fatty acid ester(s) of dextrin.

Preferably, the dextrin ester is an ester of dextrin and of a $C_{12}$-$C_{18}$ and in particular $C_{14}$-$C_{18}$ fatty acid.

Preferably, the dextrin ester is chosen from dextrin myristate and/or dextrin palmitate, and mixtures thereof.

According to a particular embodiment, the dextrin ester is dextrin myristate, especially such as the product sold under the name Rheopearl MKL-2 by the company Chiba Flour.

According to a preferred embodiment, the dextrin ester is dextrin palmitate. This product may be chosen, for example, from those sold under the names Rheopearl TL® and Rheopearl KL® by the company Chiba Flour.

The composition according to the invention may particularly preferably comprise between 0.1% and 10% by weight and preferably between 0.5% and 5% by total weight of dextrin ester(s) relative to the total weight of the composition.

The composition according to the invention may particularly preferably comprise between 0.1% and 10% by weight and preferably between 0.5% and 5% by total weight of dextrin palmitate relative to the total weight of the composition, especially such as the products sold under the names Rheopearl TL and Rheopearl KL by the company Chiba Flour.

$C_2$-$C_6$ Carboxylic Acid Ester of Sucrose

A composition according to the invention may also comprise at least one $C_2$-$C_6$ carboxylic acid ester of sucrose.

More particularly, this $C_2$-$C_6$ carboxylic acid ester of sucrose is chosen from mixed esters of acetic acid, isobutyric acid and sucrose, and in particular sucrose diacetate hexakis(2-methylpropanoate), such as the product sold under the name Sustane SAIB Food Grade Kosher by the company Eastman Chemical (INCI name: sucrose acetate isobutyrate).

Advantageously, a composition of the invention may comprise from 1% to 15% by weight and preferably from 3% to 10% by weight of $C_2$-$C_6$ carboxylic acid ester(s) of sucrose relative to the total weight of the said composition.

Moisturizer:

The composition according to the invention may comprise at least one moisturizer. Preferably, the moisturizer may be chosen from: sorbitol, polyhydric alcohols, preferably of $C_2$-$C_8$ and more preferably of $C_3$-$C_6$, preferably such as glycerol, propylene glycol, 1,3-butylene glycol, dipropylene glycol and diglycerol, and mixtures thereof.

According to a particular embodiment, the moisturizer is glycerol.

The moisturizer is preferably present in the fatty phase in a total content of between 0.1% and 10% by weight relative to the total weight of the composition.

Hydrocarbon-Based Resin

The composition according to the invention comprises at least one hydrocarbon-based resin.

Preferably, the hydrocarbon-based resin (also known as a tackifying resin) has a number-average molecular weight of less than or equal to 10 000 g/mol, especially ranging from 250 to 5000 g/mol, better still less than or equal to 2000 g/mol and especially ranging from 250 to 2000 g/mol.

The number-average molecular weights (Mn) are determined by gel permeation liquid chromatography (THF solvent, calibration curve established with linear polystyrene standards, refractometric detector).

The resin of the composition according to the invention is advantageously a tackifying resin. Such resins are described especially in the Handbook of Pressure Sensitive Adhesive Technology, edited by Donatas Satas, 3rd edition, 1989, pp.

Preferably, the hydrocarbon-based resin is chosen from low molecular weight polymers that may be classified, according to the type of monomer they comprise, as:

indene hydrocarbon-based resins, preferably such as resins derived from the polymerization in major proportion of indene monomer and in minor proportion of a monomer chosen from styrene, methylindene and methylstyrene, and mixtures thereof. These resins may optionally be hydrogenated. These resins may have a molecular weight ranging from 290 to 1150 g/mol.

Examples of indene resins that may be mentioned include those sold under the reference Escorez 7105 by the company Exxon Chem., Nevchem 100 and Nevex 100 by the company Neville Chem., Norsolene S105 by the company Sartomer, Picco 6100 by the company Hercules and Resinall by the company Resinall Corp., or the hydrogenated indene/methylstyrene/styrene copolymers sold under the name "Regalite" by the company Eastman Chemical, in particular Regalite R1100, Regalite R1090, Regalite R7100, Regalite R1010 Hydrocarbon Resin and Regalite R1125 Hydrocarbon Resin;

aliphatic pentanediene resins such as those derived from the majority polymerization of the 1,3-pentanediene (trans- or cis-piperylene) monomer and of minor monomers chosen from isoprene, butene, 2-methyl-2-butene, pentene and 1,4-pentanediene, and mixtures thereof. These resins may have a molecular weight ranging from 1000 to 2500 g/mol.

Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wingtack 86, Wingtack Extra and Wingtack Plus by the company Goodyear;

diene resins of cyclopentanediene dimers such as those derived from the polymerization of first monomers chosen from indene and styrene, and of second monomers chosen from cyclopentanediene dimers such as dicyclopentadiene, methyldicyclopentanediene and other pentanediene dimers, and mixtures thereof. These resins generally have a molecular weight ranging from 500 to 800 g/mol, for instance those sold under the reference Betaprene BR 100 by the company Arizona Chemical Co., Neville LX-685-125 and Neville LX-1000 by the company Neville Chem., Piccodiene 2215 by the company Hercules, Petro-Rez 200 by the company Lawter or Resinall 760 by the company Resinall Corp.;

diene resins of isoprene dimers such as terpenic resins derived from the polymerization of at least one monomer chosen from α-pinene, β-pinene and limonene, and mixtures thereof. These resins can have a molecular weight ranging from 300 to 2000 g/mol. Such resins are sold, for example, under the names Piccolyte A115 and 5125 by the company Hercules or Zonarez 7100 or Zonatac 105 Lite by the company Arizona Chem.

Mention may also be made of certain modified resins such as hydrogenated resins, for instance those sold under the name Eastotac C6-C20 Polyolefin by the company Eastman Chemical Co., under the reference Escorez 5300 by the company Exxon Chemicals, or the resins Nevillac Hard or Nevroz sold by the company Neville Chem., the resins Piccofyn A-100, Piccotex 100 or Piccovar AP25 sold by the company Hercules or the resin SP-553 sold by the company Schenectady Chemical Co.

According to one preferred embodiment, the hydrocarbon-based resin is chosen from indene hydrocarbon-based resins, aliphatic pentadiene resins, mixed resins of pentanediene and of indene, diene resins of cyclopentanediene dimers and diene resins of isoprene dimers, or mixtures thereof.

Preferably, the composition comprises at least one compound chosen from hydrocarbon-based resins as described previously, especially indene hydrocarbon-based resins and aliphatic pentadiene resins, or mixtures thereof. According to one preferred embodiment, the hydrocarbon-based resin is chosen from indene hydrocarbon-based resins.

According to one preferred embodiment, the resin is chosen from indene/methylstyrene/hydrogenated styrene copolymers.

In particular, use may be made of indene/methylstyrene/hydrogenated styrene copolymers, such as those sold under the name Regalite by the company Eastman Chemical, such as Regalite R 1100, Regalite R 1090, Regalite R-7100, Regalite R 1010 Hydrocarbon Resin and Regalite R 1125 Hydrocarbon Resin.

Preferably, the hydrocarbon-based resin is present in the composition according to the invention in a content ranging from 1% to 45% by weight, preferably ranging from 3% to 30% by weight and more preferentially ranging from 5% to 25% by weight relative to the total weight of the composition.

Preferably, the hydrocarbon-based resin is present in the composition according to the invention in a content ranging from 5% to 25% by weight and more preferentially ranging from 8% to 20% by weight relative to the total weight of the composition.

Hydrocarbon-Based Block Copolymer

Preferably, the composition according to the invention may comprise a hydrocarbon-based block copolymer, also known as a block copolymer, preferably a block copolymer that is soluble or dispersible in a liquid fatty phase as defined previously.

Such a compound is capable of thickening or gelling the organic phase of the composition. Preferably, the hydrocarbon-based block copolymer is an amorphous polymer, which means a polymer that does not have a crystalline form. Such a compound has film-forming properties, i.e. it is capable of forming a film when applied to the skin.

Preferably, the hydrocarbon-based block copolymer is obtained from at least one styrene monomer.

The hydrocarbon-based block copolymer may especially be a diblock, triblock, multiblock, radial or star copolymer, or mixtures thereof.

Such hydrocarbon-based block copolymers are described in patent application US-A-2002/005 562 and in U.S. Pat. No. 5,221,534.

The copolymer may contain at least one block whose glass transition temperature is preferably less than 20° C., preferably less than or equal to 0° C., preferably less than or equal to −20° C. and more preferably less than or equal to −40° C. The glass transition temperature of the said block may be between −150° C. and 20° C. and especially between −100° C. and 0° C.

The hydrocarbon-based block copolymer present in the composition according to the invention is an amorphous copolymer formed by polymerization of an olefin. The olefin may especially be an elastomeric ethylenically unsaturated monomer.

Examples of olefins that may be mentioned include ethylenic carbide monomers, especially containing one or two ethylenic unsaturations and containing from 2 to 5 carbon atoms, such as ethylene, propylene, butadiene, isoprene or pentadiene.

Advantageously, the hydrocarbon-based block copolymer is an amorphous block copolymer of styrene and of olefin.

Block copolymers comprising at least one styrene block and at least one block comprising units chosen from butadiene, ethylene, propylene, butylene and isoprene or a mixture thereof are especially preferred.

According to one preferred embodiment, the hydrocarbon-based block copolymer is hydrogenated to reduce the residual ethylenic unsaturations after the polymerization of the monomers.

In particular, the hydrocarbon-based block copolymer is a copolymer, optionally hydrogenated, containing styrene blocks and ethylene/C3-C4 alkylene blocks.

According to one preferred embodiment, the composition according to the invention comprises at least one diblock copolymer, which is preferably hydrogenated, preferably chosen from styrene-ethylene/propylene copolymers, styrene-ethylene/butadiene copolymers and styrene-ethylene/butylene copolymers. The diblock polymers are especially sold under the name Kraton® G1701E by the company Kraton Polymers.

According to another preferred embodiment, the composition according to the invention comprises at least one triblock copolymer, which is preferably hydrogenated, preferably chosen from styrene-ethylene/propylene-styrene copolymers, styrene-ethylene/butadiene-styrene copolymers, styrene-isoprene-styrene copolymers and styrene-butadiene-styrene copolymers. Triblock polymers are especially sold under the names Kraton® G1650, Kraton® G1652, Kraton® D1101, Kraton® D1102 and Kraton® D1160 by the company Kraton Polymers.

According to one embodiment of the present invention, the hydrocarbon-based block copolymer is a styrene-ethylene/butylene-styrene triblock copolymer.

According to one preferred embodiment of the invention, it is especially possible to use a mixture of a styrene-butylene/ethylene-styrene triblock copolymer and of a styrene-ethylene/butylene diblock copolymer, especially the products sold under the name Kraton® G1657M by the company Kraton Polymers.

According to another preferred embodiment, the composition according to the invention comprises a mixture of styrene-butylene/ethylene-styrene hydrogenated triblock copolymer and of ethylene-propylene-styrene hydrogenated star polymer, such a mixture possibly being especially in isododecane or in another oil. Such mixtures are sold, for example, by the company Penreco under the trade names Versagel® M5960 and Versagel® M5670.

Advantageously, a diblock copolymer such as those described previously is used as polymeric gelling agent, in particular a styrene-ethylene/propylene diblock copolymer or a mixture of diblock and triblock copolymers, as described previously.

The hydrocarbon-based block copolymer (or the mixture of hydrocarbon-based block copolymers) may be present in a content ranging from 0.1% to 15% by weight and preferably ranging from 0.5% to 10% by weight relative to the total weight of the composition.

Preferably, when the composition is in liquid form, the hydrocarbon-based block copolymer is present in the composition according to the invention in a content ranging from 3% to 15% by weight and more preferentially ranging from 5% to 10% by weight relative to the total weight of the composition.

Preferably, the weight ratio of the hydrocarbon-based resin to the hydrocarbon-based block copolymer is between 1 and 10.

More preferably, the weight ratio of the hydrocarbon-based resin to the hydrocarbon-based block copolymer is between 1 and 8.

More preferably, when the composition is in liquid form, the weight ratio of the hydrocarbon-based resin to the hydrocarbon-based block copolymer is between 1 and 5 and preferably between 1 and 3.

More preferably, when the composition is in solid form, the weight ratio of the hydrocarbon-based resin to the hydrocarbon-based block copolymer is between 2 and 8 and preferably between 3 and 5.

Block Ethylenic Copolymer

According to one embodiment, the composition according to the present invention may comprise at least one block ethylenic copolymer (also known as a block ethylenic polymer), containing at least a first block with a glass transition temperature (Tg) of greater than or equal to 40° C. and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., the said first block and the said second block being connected together via a statistical intermediate segment comprising at least one of the said first constituent monomers of the first block and at least one of the said second constituent monomers of the second block, and the said block copolymer having a polydispersity index I of greater than 2.

The block polymer used according to the invention thus comprises at least a first block and at least a second block.

The term "at least one block" means one or more blocks.

The term "block polymer" means a polymer comprising at least two different blocks and preferably at least three different blocks.

The term "ethylenic" polymer means a polymer obtained by polymerization of ethylenically unsaturated monomers.

The block ethylenic polymer used according to the invention is prepared exclusively from monofunctional monomers.

This means that the block ethylenic polymer used according to the present invention does not contain any multifunctional monomers, which make it possible to break the linearity of a polymer so as to obtain a branched or even crosslinked polymer, as a function of the content of multifunctional monomer. The polymer used according to the invention does not, either, contain any macromonomers (the term "macromonomer" means a monofunctional monomer containing a pendent group of polymeric nature, and preferably having a molecular mass of greater than 500 g/mol, or alternatively a polymer comprising on only one of its ends a polymerizable (or ethylenically unsaturated) end group), which are used in the preparation of a grafted polymer.

It is pointed out that, in the text hereinabove and hereinbelow, the terms "first" and "second" blocks do not in any way condition the order of the said blocks in the structure of the polymer.

The first block and the second block of the polymer used in the invention may be advantageously mutually incompatible.

The term "mutually incompatible blocks" means that the mixture formed from a polymer corresponding to the first block and from a polymer corresponding to the second block is not miscible in the polymerization solvent that is in major amount by weight for the block polymer, at room temperature (25° C.) and atmospheric pressure ($10^5$ Pa), for a content of the mixture of the said polymers of greater than or equal to 5% by weight, relative to the total weight of the mixture of the said polymers and of the said polymerization solvent, it being understood that:

i) the said polymers are present in the mixture in a content such that the respective weight ratio ranges from 10/90 to 90/10, and that ii) each of the polymers corresponding to the first and second blocks has an average (weight-average or number-average) molecular mass equal to that of the block polymer±15%.

In the case of a mixture of polymerization solvents, and in the event that two or more solvents are present in identical mass proportions, the said polymer mixture is immiscible in at least one of them.

Needless to say, in the case of a polymerization performed in a single solvent, this solvent is the solvent that is in major amount.

The block polymer according to the invention comprises at least a first block and at least a second block that are connected together via an intermediate segment comprising at least one constituent monomer of the first block and at least one constituent monomer of the second block. The intermediate segment (also known as the intermediate block) has a glass transition temperature Tg that is between the glass transition temperatures of the first and second blocks.

The intermediate block is a block comprising at least one constituent monomer of the first block and at least one constituent monomer of the second block of the polymer, which enables these blocks to be "compatibilized".

Advantageously, the intermediate segment comprising at least one constituent monomer of the first block and at least one constituent monomer of the second block of the polymer is a statistical polymer.

Preferably, the intermediate block is derived essentially from constituent monomers of the first block and of the second block.

The term "essentially" means at least 85%, preferably at least 90%, better still 95% and even better still 100%.

The block polymer according to the invention is advantageously a film-forming block ethylenic polymer.

The term "ethylenic" polymer means a polymer obtained by polymerization of ethylenically unsaturated monomers.

The term "film-forming polymer" means a polymer that is capable of forming, by itself or in the presence of an auxiliary film-forming agent, a continuous deposit on a support, especially on keratin materials.

Preferentially, the polymer according to the invention does not comprise any silicon atoms in its backbone. The term "backbone" means the main chain of the polymer, as opposed to the pendent side chains.

Preferably, the polymer according to the invention is not water-soluble, i.e. the polymer is not soluble in water or in a mixture of water and linear or branched lower monoalcohols containing from 2 to 5 carbon atoms, for instance ethanol, isopropanol or n-propanol, without modifying the pH, at an active material content of at least 1% by weight, at room temperature (25° C.).

Preferably, the polymer according to the invention is not an elastomer.

The term "non-elastomeric polymer" means a polymer which, when it is subjected to a constraint intended to pull it (for example by 30% relative to its initial length), does not return to a length substantially identical to its initial length when the constraint ceases.

More specifically, the term "non-elastomeric polymer" denotes a polymer with an instantaneous recovery $R_i$<50% and a delayed recovery $R_{2h}$<70% after having been subjected to a 30% elongation. Preferably, $R_i$ is <30% and $R_{2h}$<50%.

More specifically, the non-elastomeric nature of the polymer is determined according to the following protocol:

A polymer film is prepared by pouring a solution of the polymer in a Teflon-coated mould, followed by drying for 7 days in an environment conditioned at 23±5° C. and 50±10% relative humidity.

A film about 100 μm thick is thus obtained, from which are cut rectangular specimens (for example using a punch) 15 mm wide and 80 mm long.

This sample is subjected to a tensile stress using a machine sold under the reference Zwick, under the same temperature and humidity conditions as for the drying.

The specimens are pulled at a speed of 50 mm/min and the distance between the jaws is 50 mm, which corresponds to the initial length ($l_0$) of the specimen.

The instantaneous recovery $R_i$ is determined in the following manner
- the specimen is pulled by 30% ($\epsilon_{max}$), i.e. about 0.3 times its initial length ($l_o$)
- the constraint is released by applying a return speed equal to the tensile speed, i.e. 50 mm/min, and the residual elongation of the specimen is measured as a percentage, after returning to zero constraint ($\epsilon i$).

The percentage instantaneous recovery ($R_i$) is given by the following formula:

$$R_i = (\epsilon_{max} - \epsilon_i)/\epsilon_{max} \times 100$$

To determine the delayed recovery, the percentage residual elongation of the specimen after 2 hours ($_{2h}$) is measured (2 hours after returning to zero stress load).

The percentage delayed recovery ($R_{2h}$) is given by the following formula:

$$R_{2h} = (\epsilon_{max} - \epsilon_{2h})/\epsilon_{max} \times 100$$

Purely as a guide, a polymer according to one embodiment of the invention has an instantaneous recovery $R_i$ of 10% and a delayed recovery $R_{2h}$ of 30%.

The polydispersity index of the polymer of the invention is greater than 2.

Advantageously, the block polymer used in the compositions according to the invention has a polydispersity index I of greater than 2, for example ranging from 2 to 9, preferably greater than or equal to 2.5, for example ranging from 2.5 to 8 and better still greater than or equal to 2.8, and especially ranging from 2.8 to 6.

The polydispersity index I of the polymer is equal to the ratio of the weight-average mass Mw to the number-average mass Mn.

The weight-average molar mass (Mw) and number-average molar mass (Mn) are determined by gel permeation liquid chromatography (THF solvent, calibration curve established with linear polystyrene standards, refractometric detector).

The weight-average mass (Mw) of the polymer according to the invention is preferably less than or equal to 300 000; it ranges, for example, from 35 000 to 200 000 and better still from 45 000 to 150 000 g/mol.

The number-average mass (Mn) of the polymer according to the invention is preferably less than or equal to 70 000; it ranges, for example, from 10 000 to 60 000 and better still from 12 000 to 50 000 g/mol.

Preferably, the polydispersity index of the polymer according to the invention is advantageously greater than 2, for example ranging from 2 to 9, preferably greater than or equal to 2.5, for example ranging from 2.5 to 8, and better still greater than or equal to 2.8, especially from 2.8 to 6.

First Block with a Tg of Greater than or Equal to 40° C.

The block with a Tg of greater than or equal to 40° C. has, for example, a Tg ranging from 40° C. to 150° C., preferably greater than or equal to 50° C., for example ranging from 50° C. to 120° C. and better still greater than or equal to 60° C., for example ranging from 60° C. to 120° C.

The glass transition temperatures indicated for the first and second blocks may be theoretical Tg values determined from the theoretical Tg values of the constituent monomers of each of the blocks, which may be found in a reference manual such as the Polymer Handbook, 3rd Edition, 1989, John Wiley, according to the following relationship, known as Fox's law:

$$1/Tg = \sum_i (\varpi_i/Tg_i),$$

$\varpi_i$ being the mass fraction of the monomer i in the block under consideration and $Tg_i$ being the glass transition temperature of the homopolymer of the monomer i.

Unless otherwise indicated, the Tg values indicated for the first and second blocks in the present patent application are theoretical Tg values.

The difference between the glass transition temperatures of the first and second blocks is generally greater than 10° C., preferably greater than 20° C. and better still greater than 30° C.

In the present invention, the expression: "between . . . and . . . " is intended to denote a range of values for which the limits mentioned are excluded, and "from . . . to . . . " and "ranging from . . . to . . . " are intended to denote a range of values for which the limits are included.

The block with a Tg of greater than or equal to 40° C. may be a homopolymer or a copolymer.

The block with a Tg of greater than or equal to 40° C. may be derived totally or partially from one or more monomers which are such that the homopolymer prepared from these monomers has a glass transition temperature of greater than or equal to 40° C. This block may also be referred to as a "rigid block".

In the case where this block is a homopolymer, it is derived from monomers which are such that the homopolymers prepared from these monomers have glass transition temperatures of greater than or equal to 40° C. This first block may be a homopolymer consisting of only one type of monomer (for which the Tg of the corresponding homopolymer is greater than or equal to 40° C.).

In the case where the first block is a copolymer, it may be totally or partially derived from one or more monomers, the nature and concentration of which are chosen such that the Tg of the resulting copolymer is greater than or equal to 40° C. The copolymer may comprise, for example:

- monomers which are such that the homopolymers prepared from these monomers have Tg values of greater than or equal to 40° C., for example a Tg ranging from 40° C. to 150° C., preferably greater than or equal to 50° C., for example ranging from 50° C. to 120° C. and better still greater than or equal to 60° C., for example ranging from 60° C. to 120° C., and
- monomers which are such that the homopolymers prepared from these monomers have Tg values of less than 40° C., chosen from monomers with a Tg of between 20° C. and 40° C. and/or monomers with a Tg of less than or equal to 20° C., for example a Tg ranging from −100° C. to 20° C., preferably less than 15° C., especially ranging from −80° C. to 15° C. and better still less than 10° C., for example ranging from −50° C. to 0° C., as described later.

The first monomers whose homopolymers have a glass transition temperature of greater than or equal to 40° C. are chosen, preferably, from the following monomers, also known as the main monomers:

the methacrylates of formula $CH_2=C(CH_3)-COOR_1$ in which $R_1$ represents a linear or branched unsubstituted alkyl group containing from 1 to 4 carbon atoms, such as a methyl, ethyl, propyl or isobutyl group or $R_1$ represents a $C_4$ to $C_{12}$ cycloalkyl group, preferably a $C_8$ to $C_{12}$ cycloalkyl, such as isobornyl methacrylate, the acrylates of formula $CH_2=CH-COOR_2$ in which $R_2$ represents a $C_4$ to $C_{12}$ cycloalkyl group such as an isobornyl group or a tert-butyl group, the (meth)acrylamides of formula:

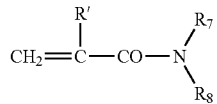

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. Examples of monomers that may be mentioned include N-butylacrylamide, N-tert-butylacrylamide, N-isopropylacrylamide, N,N-dimethylacrylamide and N,N-dibutylacrylamide, and their mixtures.

The first block is advantageously obtained from at least one acrylate monomer of formula $CH_2=CH-COOR_2$ and from at least one methacrylate monomer of formula $CH_2=C(CH_3)-COOR_2$ in which $R_2$ represents a $C_4$ to $C_{12}$ cycloalkyl group, preferably a $C_8$ to $C_{12}$ cycloalkyl, such as isobornyl. The monomers and the proportions thereof are preferably chosen such that the glass transition temperature of the first block is greater than or equal to 40° C.

According to one embodiment, the first block is obtained from:
i) at least one acrylate monomer of formula $CH_2=CH-COOR_2$ in which $R_2$ represents a $C_4$ to $C_{12}$ cycloalkyl group, preferably a $C_8$ to $C_{12}$ cycloalkyl group, such as isobornyl,
ii) and at least one methacrylate monomer of formula $CH_2=C(CH_3)-COOR'_2$ in which $R'_2$ represents a $C_4$ to $C_{12}$ cycloalkyl group, preferably a $C_8$ to $C_{12}$ cycloalkyl group, such as isobornyl.

According to one embodiment, the first block is obtained from at least one acrylate monomer of formula $CH_2=CH-COOR_2$ in which $R_2$ represents a $C_8$ to $C_{12}$ cycloalkyl group, such as isobornyl, and from at least one methacrylate monomer of formula $CH_2=C(CH_3)-COOR'_2$ in which $R'_2$ represents a $C_8$ to $C_{12}$ cycloalkyl group, such as isobornyl.

Preferably, $R_2$ and $R'_2$ represent, independently or simultaneously, an isobornyl group.

Preferably, the block copolymer comprises from 50% to 80% by weight of isobornyl methacrylate/acrylate, from 10% to 30% by weight of isobutyl acrylate and from 2% to 10% by weight of acrylic acid.

The first block may be obtained exclusively from the said acrylate monomer and from the said methacrylate monomer.

The acrylate monomer and the methacrylate monomer are preferably in mass proportions of between 30/70 and 70/30, preferably between 40/60 and 60/40 and especially of the order of 50/50.

The proportion of the first block advantageously ranges from 20% to 90%, better still from 30% to 80% and even better still from 60% to 80% by weight of the polymer.

According to one embodiment, the first block is obtained by polymerization of isobornyl methacrylate and isobornyl acrylate.

Second Block with a Glass Transition Temperature of Less than 20° C.

The second block advantageously has a glass transition temperature Tg of less than or equal to 20° C., for example a Tg ranging from −100° C. to 20° C., preferably less than or equal to 15° C., especially ranging from −80° C. to 15° C. and better still less than or equal to 10° C., for example ranging from −100° C. to 10° C., especially ranging from −30° C. to 10° C.

The second block is totally or partially derived from one or more second monomers, which are such that the homopolymer prepared from these monomers has a glass transition temperature of less than or equal to 20° C.

This block may also be referred to as a "flexible block".

The monomer with a Tg of less than or equal to 20° C. (known as the second monomer) is preferably chosen from the following monomers:

the acrylates of formula $CH_2=CHCOOR_3$ $R_3$ representing a linear or branched $C_1$ to $C_{12}$ unsubstituted alkyl group, with the exception of the tert-butyl group, in which one or more heteroatoms chosen from O, N and S are optionally intercalated, the methacrylates of formula $CH_2=C(CH_3)-COOR_4$ $R_4$ representing a linear or branched $C_6$ to $C_{12}$ unsubstituted alkyl group, in which one or more heteroatoms chosen from O, N and S are optionally intercalated;

the vinyl esters of formula $R_5-CO-O-CH=CH_2$ in which $R_5$ represents a linear or branched $C_4$ to $C_{12}$ alkyl group;

ethers of vinyl alcohol and of a $C_4$ to $C_{12}$ alcohol, $N-(C_4$ to $C_{12})$alkyl acrylamides, such as N-octylacrylamide, and their mixtures.

The preferred monomers with a Tg of less than or equal to 20° C. are isobutyl acrylate, 2-ethylhexyl acrylate or mixtures thereof in all proportions.

Each of the first and second blocks may contain in small proportion at least one constituent monomer of the other block.

Thus, the first block may contain at least one constituent monomer of the second block, and vice versa.

Each of the first and/or second blocks may comprise, in addition to the monomers indicated above, one or more other monomers known as additional monomers, which are different from the main monomers mentioned above.

The nature and amount of this or these additional monomer(s) are chosen such that the block in which they are present has the desired glass transition temperature.

This additional monomer is chosen, for example, from:
ethylenically unsaturated monomers comprising at least one tertiary amine function, for instance 2-vinylpyridine, 4-vinylpyridine, dimethylaminoethyl methacrylate, diethylaminoethyl methacrylate and dimethylaminopropylmethacrylamide, and salts thereof, the methacrylates of formula $CH_2=C(CH_3)-COOR_6$ in which $R_6$ represents a linear or branched alkyl group containing from 1 to 4 carbon atoms, such as a methyl, ethyl, propyl or isobutyl group, the said alkyl group being substituted with one or more substituents chosen from hydroxyl groups (for instance 2-hydroxypropyl methacrylate and 2-hydroxyethyl methacrylate) and halogen atoms (Cl, Br, I or F), such as trifluoroethyl methacrylate, the methacrylates of formula $CH_2=C(CH_3)—COOR_9$ $R_9$ representing a linear or branched $C_6$ to $C_{12}$ alkyl group in which one or more heteroatoms chosen from O, N and S is (are) optionally intercalated, the said alkyl group being substituted with one or more substituents chosen from hydroxyl groups and halogen atoms (Cl, Br, I or F);

acrylates of formula $CH_2=CHCOOR_{10}$, $R_{10}$ representing a linear or branched $C_1$ to $C_{12}$ alkyl group substituted with one or more substituents chosen from hydroxyl groups and halogen atoms (Cl, Br, I or F), such as 2-hydroxypropyl acrylate and 2-hydroxyethyl acrylate, or $R_{10}$ represents a $C_1$ to $C_{12}$ alkyl-O-POE (polyoxyethylene) with repetition of the oxyethylene unit 5 to 10 times, for example methoxy-POE, or $R_{10}$ represents a polyoxyethylenated group comprising from 5 to 10 ethylene oxide units.

In particular, the first block may comprise as additional monomer:

(meth)acrylic acid, preferably acrylic acid, tert-butyl acrylate, the methacrylates of formula $CH_2=C(CH_3)—COOR_1$ in which $R_1$ represents a linear or branched unsubstituted alkyl group containing from 1 to 4 carbon atoms, such as a methyl, ethyl, propyl or isobutyl group, the (meth)acrylamides of formula:

in which $R_7$ and $R_8$, which may be identical or different, each represent a hydrogen atom

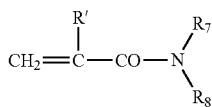

or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. Examples of monomers that may be mentioned include N-butylacrylamide, N-tert-butylacrylamide, N-isopropylacrylamide, N,N-dimethylacrylamide and N,N-dibutylacrylamide, and mixtures thereof.

The additional monomer may represent 0.5% to 30% by weight relative to the weight of the polymer. According to one embodiment, the polymer of the invention does not contain any additional monomer.

Preferably, the polymer of the invention comprises at least isobornyl acrylate and isobornyl methacrylate monomers in the first block and isobutyl acrylate and acrylic acid monomers in the second block.

Preferably, the polymer comprises at least isobornyl acrylate and isobornyl methacrylate monomers in equivalent weight proportion in the first block and isobutyl acrylate and acrylic acid monomers in the second block.

Preferably, the polymer comprises at least isobornyl acrylate and isobornyl methacrylate monomers in equivalent weight proportion in the first block and isobutyl acrylate and acrylic acid monomers in the second block, the first block representing 70% by weight of the polymer.

Preferably, the polymer comprises at least isobornyl acrylate and isobornyl methacrylate monomers in equivalent weight proportion in the first block and isobutyl acrylate and acrylic acid monomers in the second block. Preferably, the block with a Tg of greater than 40° C. represents 70% by weight of the polymer, and acrylic acid represents 5% by weight of the polymer.

According to one embodiment, the first block does not comprise any additional monomer.

According to a preferred embodiment, the second block comprises acrylic acid as additional monomer. In particular, the second block is advantageously obtained from an acrylic acid monomer and from at least one other monomer with a Tg of less than or equal to 20° C.

According to a preferred embodiment, the composition according to the invention comprises at least one copolymer comprising at least one acrylate monomer of formula $CH_2=CH—COOR_2$ in which $R_2$ represents a $C_8$ to $C_{12}$ cycloalkyl group, and/or at least one methacrylate monomer of formula $CH_2=C(CH_3)—COOR'_2$ in which $R'_2$ represents a $C_8$ to $C_{12}$ cycloalkyl group, at least a second acrylate monomer of formula $CH_2=CHCOOR_3$, in which $R_3$ represents an unsubstituted, linear or branched $C_1$ to $C_{12}$ alkyl group, with the exception of a tert-butyl group, and at least one acrylic acid monomer.

Preferably, the copolymer used in the compositions according to the invention is obtained from at least one isobornyl methacrylate monomer, at least one isobornyl acrylate monomer, at least one isobutyl acrylate monomer and at least one acrylic acid monomer.

Advantageously, the copolymer in the invention comprises from 50% to 80% by weight of isobornyl methacrylate/acrylate mixture, from 10% to 30% by weight of isobutyl acrylate and from 2% to 10% by weight of acrylic acid.

The block copolymer may advantageously comprise more than 2% by weight of acrylic acid monomers, and especially from 2% to 15% by weight, for example from 3% to 15% by weight, in particular from 4% to 15% by weight or even from 4% to 10% by weight of acrylic acid monomers, relative to the total weight of the said copolymer.

The constituent monomers of the second block and the proportions thereof are chosen such that the glass transition temperature of the second block is less than or equal to 20° C.

Intermediate Segment

The intermediate segment (also known as the intermediate block) connects the first block and the second block of the polymer used according to the present invention. The intermediate segment results from the polymerization:

i) of the first monomer(s), and optionally of the additional monomer(s), which remain available after their polymerization to a maximum degree of conversion of 90% to form the first block, ii) and of the second monomer(s), and optionally of the additional monomer(s), added to the reaction mixture.

The formation of the second block is initiated when the first monomers no longer react or are no longer incorporated into the polymer chain either because they are all consumed or because their reactivity no longer allows them to be.

Thus, the intermediate segment comprises the first available monomers, resulting from a degree of conversion of these first monomers of less than or equal to 90%, during the introduction of the second monomer(s) during the synthesis of the polymer.

The intermediate segment of the block polymer is a statistical polymer (which may also be referred to as a statistical block). This means that it comprises a statistical distribution of the first monomer(s) and of the second monomer(s) and also of the additional monomer(s) that may be present.

Thus, the intermediate segment is a statistical block, as are the first block and the second block if they are not homopolymers (i.e. if they are both formed from at least two different monomers).

Process for Preparing the Copolymer:

The block ethylenic copolymer according to the invention is prepared by free radical polymerization, according to the techniques that are well known for this type of polymerization.

The free radical polymerization is performed in the presence of an initiator whose nature is adapted, in a known manner, as a function of the desired polymerization temperature and of the polymerization solvent. In particular, the initiator may be chosen from initiators bearing a peroxide function, redox couples or other free radical polymerization initiators known to those skilled in the art.

In particular, examples of initiators bearing a peroxide function that may be mentioned include:
  a. peroxyesters such as tert-butyl peroxyacetate, tert-butyl perbenzoate, tert-butyl peroxy-2-ethylhexanoate (Trigonox 21S from Akzo Nobel) or 2,5-bis(2-ethylhexanoylperoxy)-2,5-dimethylhexane (Trigonox 141 from Akzo Nobel);
  b. peroxydicarbonates such as diisopropyl peroxydicarbonate;
  c. peroxy ketones such as methyl ethyl ketone peroxide;
  d. hydroperoxides such as aqueous hydrogen peroxide solution ($H_2O_2$) or tert-butyl hydroperoxide;
  e. diacyl peroxides such as acetyl peroxide or benzoyl peroxide;
  f. dialkyl peroxides such as di-tert-butyl peroxide;
  g. inorganic peroxides such as potassium peroxodisulfate ($K_2S_2O_8$).

As initiator in the form of a redox couple, mention may be made of the potassium thiosulfate+potassium peroxodisulfate couple, for example.

According to a preferred embodiment, the initiator is chosen from organic peroxides comprising from 8 to 30 carbon atoms. Preferably, the initiator used is 2,5-bis(2-ethylhexanoylperoxy)-2,5-dimethylhexane sold under the reference Trigonox® 141 by the company Akzo Nobel.

The block copolymer used according to the invention is prepared by free radical polymerization and not by controlled or living polymerization. In particular, the polymerization of the block ethylenic copolymer is performed in the absence of control agents, and in particular in the absence of control agents conventionally used in living or controlled polymerization processes, such as nitroxides, alkoxyamines, dithioesters, dithiocarbamates, dithiocarbonates or xanthates, trithiocarbonates or copper-based catalysts, for example.

As mentioned previously, the intermediate segment is a statistical block, as are the first block and the second block if they are not homopolymers (i.e. if they are both formed from at least two different monomers).

The block copolymer may be prepared by free radical polymerization, and in particular via a process that consists in mixing, in the same reactor, a polymerization solvent, an initiator, at least one monomer with a glass transition temperature of greater than or equal to 40° C., at least one monomer with a glass transition temperature of less than or equal to 20° C., according to the following sequence:
  some of the polymerization solvent and optionally some of the initiator and of the monomers for the first addition are poured into the reactor, and the mixture is heated to a reaction temperature of between 60 and 120° C.,
  the said at least a first monomer with a Tg of greater than or equal to 40° C. and optionally some of the initiator are then poured in, in a first addition, and the mixture is left to react for a time T corresponding to a maximum degree of conversion of the said monomers of 90%,
  further polymerization initiator and the said at least a second monomer with a glass transition temperature of less than or equal to 20° C. are then poured into the reactor, in a second addition, and the mixture is left to react for a time T' after which the degree of conversion of the said monomers reaches a plateau,
  the reaction mixture is cooled to room temperature.

Preferably, the copolymer may be prepared by free radical polymerization, in particular via a process that consists in mixing, in the same reactor, a polymerization solvent, an initiator, an acrylic acid monomer, at least one monomer with a glass transition temperature of less than or equal to 20° C., at least one acrylate monomer of formula $CH_2=CH-COOR_2$ in which $R_2$ represents a $C_4$ to $C_{12}$ cycloalkyl group and at least one methacrylate monomer of formula $CH_2=C(CH_3)-COOR'_2$ in which $R'_2$ represents a $C_4$ to $C_{12}$ cycloalkyl group, according to the following sequence of steps:
  some of the polymerization solvent and optionally some of the initiator and of the monomers for the first addition are poured into the reactor, and the mixture is heated to a reaction temperature of between 60 and 120° C.,
  the said at least one acrylate monomer of formula $CH_2=CH-COOR_2$ and the said at least one methacrylate monomer of formula $CH_2=C(CH_3)-COOR'_2$, as monomers with a Tg of greater than or equal to 40° C., and optionally some of the initiator, are then poured in, in a first addition, and the mixture is left to react for a time T corresponding to a maximum degree of conversion of the said monomers of 90%,
  further polymerization initiator, the acrylic acid monomer and the said at least one monomer with a glass transition temperature of less than or equal to 20° C. are then poured into the reactor, in a second addition, and the mixture is left to react for a time T' after which the degree of conversion of the said monomers reaches a plateau,
  the reaction mixture is cooled to room temperature.

The term "polymerization solvent" means a solvent or a mixture of solvents. In particular, as polymerization solvents that may be used, mention may be made of:
  ketones that are liquid at room temperature, such as methyl ethyl ketone, methyl isobutyl ketone, diisobutyl ketone, isophorone, cyclohexanone or acetone;
  propylene glycol ethers that are liquid at room temperature, such as propylene glycol monoethyl ether, propylene glycol monoethyl ether acetate or dipropylene glycol mono-n-butyl ether;
  short-chain esters (containing from 3 to 8 carbon atoms in total), such as ethyl acetate, methyl acetate, propyl acetate, n-butyl acetate or isopentyl acetate;
  ethers that are liquid at room temperature, such as diethyl ether, dimethyl ether or dichlorodiethyl ether;
  alkanes that are liquid at room temperature, such as decane, heptane, dodecane, isododecane, cyclohexane and isohexadecane;
  aromatic cyclic compounds that are liquid at room temperature, such as toluene and xylene; aldehydes that are liquid at room temperature, such as benzaldehyde and acetaldehyde, and mixtures thereof.

Conventionally, the polymerization solvent is a volatile oil with a flash point of less than 80° C. The flash point is measured in particular according to standard ISO 3679.

The polymerization solvent may be chosen especially from ethyl acetate, butyl acetate, alcohols such as isopropanol or ethanol, and aliphatic alkanes such as isododecane, and mixtures thereof. Preferably, the polymerization solvent is a mixture of butyl acetate and isopropanol or isododecane.

According to another embodiment, the copolymer may be prepared by free radical polymerization according to a preparation process that consists in mixing, in the same reactor, a polymerization solvent, an initiator, at least one monomer with a glass transition temperature of less than or equal to 20° C. and at least one monomer with a Tg of greater than or equal to 40° C., according to the following sequence of steps:

some of the polymerization solvent and optionally some of the initiator and of the monomers for the first addition are poured into the reactor, and the mixture is heated to a reaction temperature of between 60 and 120° C., the said at least one monomer with a glass transition temperature of less than or equal to 20° C. and optionally some of the initiator are then poured in, in a first addition, and the mixture is left to react for a time T corresponding to a maximum degree of conversion of the said monomers of 90%, further polymerization initiator and the said at least one monomer with a Tg of greater than or equal to 40° C. are then poured into the reactor, in a second addition, and the mixture is left to react for a time T' after which the degree of conversion of the said monomers reaches a plateau, the reaction mixture is cooled to room temperature.

According to a preferred embodiment, the copolymer may be prepared by free radical polymerization according to a preparation process that consists in mixing, in the same reactor, a polymerization solvent, an initiator, an acrylic acid monomer, at least one monomer with a glass transition temperature of less than or equal to 20° C., at least one monomer with a Tg of greater than or equal to 40° C., and in particular, as monomers with a Tg of greater than or equal to 40° C., at least one acrylate monomer of formula $CH_2=CH-COOR_2$ in which $R_2$ represents a $C_4$ to $C_{12}$ cycloalkyl group and at least one methacrylate monomer of formula $CH_2=C(CH_3)-COOR'_2$ in which $R'_2$ represents a $C_4$ to $C_{12}$ cycloalkyl group, according to the following sequence of steps:

some of the polymerization solvent and optionally some of the initiator and of the monomers for the first addition are poured into the reactor, and the mixture is heated to a reaction temperature of between 60 and 120° C., the acrylic acid monomer and the said at least one monomer with a glass transition temperature of less than or equal to 20° C. and optionally some of the initiator are then poured in, in a first addition, and the mixture is left to react for a time T corresponding to a maximum degree of conversion of the said monomers of 90%, further polymerization initiator, the said at least one acrylate monomer of formula $CH_2=CH-COOR_2$ and the said at least one methacrylate monomer of formula $CH_2=C(CH_3)-COOR'_2$, as monomer with a Tg of greater than or equal to 40° C., are then poured into the reactor, in a second addition, and the mixture is left to react for a time T' after which the degree of conversion of the said monomers reaches a plateau, the reaction mixture is cooled to room temperature.

The polymerization temperature is preferably about 90° C.

The reaction time after the second addition is preferably between 3 and 6 hours.

Block copolymers such as those described previously are especially described in patent applications EP-A-1 411 069 and EP-A-1 882 709.

The synthesis solvent used for the polymerization of the film-forming copolymer is generally chosen from volatile oils with a flash point of less than 80° C., for instance isododecane.

According to a particularly preferred embodiment of the invention, the composition contains a non-volatile hydrocarbon-based ester oil comprising at least 16 carbon atoms and having a molar mass of less than 650 g/mol, preferably octyldodecyl neopentanoate.

In particular, the block ethylenic copolymer may be used in the composition in the presence of this ester oil, especially during the synthesis of this block copolymer: it is thus possible to perform the process by distillation of the synthesis solvent, optionally under vacuum, and the addition of the non-volatile hydrocarbon-based ester oil.

This distillation technique is known to those skilled in the art and Example 2 described below illustrates this technique.

The distillation of the synthesis solvent (conventionally isododecane) may be performed with simultaneous addition or in the presence in the mixture, before the distillation, of a non-volatile hydrocarbon-based ester oil comprising at least 16 carbon atoms and having a molar mass of less than 650 g/mol. This step is performed at elevated temperature and optionally under vacuum to distil off a maximum amount of isododecane (and more generally of synthesis solvent), if the latter has been used as polymerization solvent, or more generally to distil off a maximum amount of volatile oil with a flash point of less than 80° C. The non-volatile ester oil may also be added partially or totally to the polymer in the volatile solvent before the distillation.

The composition according to the invention preferably comprises from 0.5% to 40% by weight of block ethylenic copolymer, advantageously from 1% to 40% by weight and especially from 2% to 30% by weight or even from 2% to 20% by weight of active material relative to the total weight of the composition.

Preferably, the composition according to the invention comprises at least 2% by weight of active material (i.e. as solids) of block ethylenic polymer, relative to the total weight of the composition.

Pulverulent Phase:

The composition according to the invention comprises at least one pulverulent phase comprising at least silica aerogel particles.

Preferably, the pulverulent phase represents between 0.1% and 25% by weight, preferably between 0.1% and 20% by weight and preferably between 0.5% and 20% by weight relative to the total weight of the composition.

Preferably, the pulverulent phase represents between 1% and 20% by weight relative to the total weight of the composition.

Besides the hydrophobic silica aerogel particles, the pulverulent phase of the composition according to the invention preferably comprises additional compounds in the form of particles.

Preferably, the pulverulent phase according to the invention may also comprise at least one additional filler other than the said hydrophobic silica aerogel particles, and/or at least one dyestuff chosen from nacres and/or pigments, and mixtures thereof.

Colourants

The composition according to the invention preferably comprises at least one colourant (also known as a colouring agent), which may be chosen from water-soluble or liposoluble dyes, pigments and nacres, and mixtures thereof.

The composition according to the invention may also comprise one or more dyestuffs chosen from water-soluble dyes and pulverulent dyestuffs, for instance pigments, nacres and glitter flakes that are well known to those skilled in the art.

In a particularly preferred manner, the composition according to the invention comprises at least one dyestuff chosen from pigments and/or nacres.

The dyestuffs may be present in the composition in a content ranging from 0.01% to 20% by weight, relative to the weight of the composition, preferably from 0.1% to 15% by weight.

The term "pigments" should be understood as meaning white or coloured, mineral or organic particles that are insoluble in an aqueous solution, which are intended to colour and/or opacify the resulting film.

The pigments may be present in a proportion of from 0.01% to 20% by weight, especially from 0.1% to 15% by weight and in particular from 0.2% to 10% by weight, relative to the total weight of the cosmetic composition.

As inorganic pigments that may be used in the invention, mention may be made of titanium oxide, zirconium oxide or cerium oxide, and also zinc oxide, iron oxide or chromium oxide, ferric blue, manganese violet, ultramarine blue and chromium hydrate.

The pigment may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

The colorant may also comprise a pigment with a structure that may be, for example, of silica microspheres containing iron oxide type. An example of a pigment having this structure is the product sold by the company Miyoshi under the reference PC Ball PC-LL-100 P, this pigment being constituted of silica microspheres containing yellow iron oxide.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPPs) described in documents EP-A-542 669, EP-A-787 730, EP-A-787 731 and WO-A-96/08537.

The terms "nacres" should be understood as meaning coloured particles of any form, which may or may not be iridescent, especially produced by certain molluscs in their shell, or alternatively synthesized, and which have a colour effect via optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superimposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres sold by the company Eckart, and the Sunshine synthetic mica-based nacres sold by the company Sun Chemical.

The nacres may more particularly have a yellow, pink, red, bronze, orange, brown, gold and/or coppery colour or glint.

As illustrations of nacres that may be used in the context of the present invention, mention may be made in particular of gold-coloured nacres sold especially by the company Engelhard under the names Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona) and by the company Engelhard under the name Super bronze (Cloisonne); the orange nacres sold especially by the company Engelhard under the names Orange 363C (Cloisonne) and Orange MCR 101 (Cosmica) and by the company Merck under the names Passion orange (Colorona) and Matte orange (17449) (Microna); the brown-tinted nacres sold especially by the company Engelhard under the names Nu-antique copper 340XB (Cloisonne) and Brown CL4509 (Chromalite); the nacres with a copper glint sold especially by the company Engelhard under the name Copper 340A (Timica); the nacres with a red glint sold especially by the company Merck under the name Sienna fine (17386) (Colorona); the nacres with a yellow glint sold especially by the company Engelhard under the name Yellow (4502) (Chromalite); the red-tinted nacres with a golden glint sold especially by the company Engelhard under the name Sunstone G012 (Gemtone); the pink nacres sold especially by the company Engelhard under the name Tan opale G005 (Gemtone); the black nacres with a golden glint sold especially by the company Engelhard under the name Nu antique bronze 240 AB (Timica); the blue nacres sold especially by the company Merck under the name Matte blue (17433) (Microna); the white nacres with a silvery glint sold especially by the company Merck under the name Xirona Silver; and the golden-green pinkish-orange nacres sold especially by the company Merck under the name Indian summer (Xirona), and mixtures thereof.

Preferably, the pigments and/or nacres may be present in the composition in a total content ranging from 0.01% to 20% by weight, relative to the weight of the composition, preferably from 0.1% to 15% by weight.

The term "dyes" should be understood as meaning compounds that are generally organic, which are soluble in fatty substances such as oils or in an aqueous-alcoholic phase.

The cosmetic composition according to the invention may also comprise water-soluble or liposoluble dyes. The liposoluble dyes are, for example, Sudan red, DC Red 17, DC Green 6, β-carotene, Sudan brown, DC Yellow 11, DC Violet 2, DC Orange 5 and quinoline yellow. The water-soluble dyes are, for example, beetroot juice or methylene blue.

The cosmetic composition according to the invention may also contain at least one material with a specific optical effect as dyestuff.

This effect is different from a simple conventional hue effect, i.e. a unified and stabilized effect as produced by standard dyestuffs, for instance monochromatic pigments. For the purposes of the invention, the term "stabilized" means lacking an effect of variability of the colour as a function of the angle of observation or alternatively in response to a temperature change.

For example, this material may be chosen from particles with a metallic tint, goniochromatic colouring agents, diffracting pigments, thermochromic agents, optical brighteners, and also fibres, especially interference fibres. Needless to say, these various materials may be combined so as to afford the simultaneous manifestation of two effects, or even of a novel effect in accordance with the invention.

Fillers

A composition according to the invention may contain, besides the hydrophobic aerogel particles, at least one or more additional filler(s) other than the said hydrophobic aerogel particles.

The term "fillers" should be understood as meaning colourless or white, mineral or synthetic particles of any shape, which are insoluble in the medium of the composition, irrespective of the temperature at which the composition is manufactured. These fillers serve especially to modify the rheology or the texture of the composition.

The fillers may be mineral or organic and of any shape, platelet-shaped, spherical or oblong, irrespective of the crystallographic form (for example lamellar, cubic, hexagonal, orthorhombic, etc.).

Preferably, the said additional filler(s) are chosen from talc, mica, silica, kaolin, bentone, fumed silica particles, optionally hydrophilic- or hydrophobic-treated, polyamide (Nylon®) powder (Orgasol® from Atochem), poly-β-alanine powder and polyethylene powder, tetrafluoroethylene polymer (Teflon®) powder, lauroyllysine, starch, boron nitride, hollow polymer microspheres such as polyvinylidene chloride/acrylonitrile microspheres, for instance Expancel® (Nobel Industrie), acrylic acid copolymer microspheres (Polytrap® from the company Dow Corning), silicone resin microbeads (for example Tospearls® from Toshiba), precipitated calcium carbonate, magnesium carbonate, magnesium hydrogen carbonate, hydroxyapatite, hollow silica microspheres (Silica Beads® from Maprecos), elastomeric polyorganosiloxane particles, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

Preferably, the said additional filler(s) are chosen from talc, mica, silica, kaolin, bentone, polyamide (Nylon®) powder (Orgasol® from Atochem), poly-β-alanine powder and polyethylene powder, tetrafluoroethylene polymer (Teflon®) powder, lauroyllysine, starch, boron nitride, hollow polymer microspheres such as polyvinylidene chloride/acrylonitrile microspheres, for instance Expancel® (Nobel Industrie), acrylic acid copolymer microspheres (Polytrap® from the company Dow Corning), silicone resin microbeads (for example Tospearls® from Toshiba), precipitated calcium carbonate, magnesium carbonate, magnesium hydrogen carbonate, hydroxyapatite, hollow silica microspheres (Silica Beads® from Maprecos), elastomeric polyorganosiloxane particles, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

According to a preferred embodiment, the composition according to the invention may comprise at least one lipophilic clay.

Lipophilic clays that may preferably be used include hectorites modified with a $C_{10}$ to $C_{22}$ ammonium chloride, for instance hectorite modified with distearyldimethylammonium chloride, for instance the product sold under the name Bentone 38V® by the company Elementis.

Advantageously, a composition according to the invention comprises at least one lipophilic clay (such as hectorite modified with distearyldimethylammonium chloride) as additional filler, especially in a total content ranging from 0.1% to 15%, in particular from 0.5% to 10% and more particularly from 1% to 10% by weight relative to the total weight of the composition.

Particles comprising a copolymer, the said copolymer comprising trimethylol hexyl lactone, may also be used as additional filler. In particular, it may be a copolymer of hexamethylene diisocyanate/trimethylol hexyl lactone. Such particles are especially commercially available, for example, under the name Plastic Powder D-400® or Plastic Powder D-800® from the company Toshiki.

According to a particular embodiment, the composition according to the invention may comprise fumed silica particles, which have optionally been hydrophilic- or hydrophobic-treated, as additional filler. Preferably, the composition comprises at least one filler known as Silica Dimethyl Silylate (according to the CTFA).

The hydrophobic groups may especially be dimethylsilyloxyl or polydimethylsiloxane groups, which are especially obtained by treating fumed silica in the presence of polydimethylsiloxane or dimethyldichlorosilane. Silicas thus treated are known as Silica Dimethyl Silylate according to the CTFA (6th edition, 1995). They are sold, for example, under the references Aerosil R972® and Aerosil R974® by the company Degussa and Cab-O-Sil TS-610® and Cab-O-Sil TS-720® by the company Cabot.

These particles are conventionally of nanometric size and may be referred to as "nanosilicas".

According to a particularly preferred embodiment, the composition is free of fumed silica particles, which have especially been hydrophobic-treated. In particular, according to a particular embodiment, the composition is free of fumed silica particles whose INCI name is Silica Dimethyl Silylate.

According to a particularly preferred embodiment, the composition according to the invention is free of nanometric-size silica.

Preferably, the composition contains between 0.1% and 20% by weight and in particular between 0.1% and 15% by total weight of fillers (i.e. of hydrophobic silica aerogel particles+additional fillers), relative to the total weight of the composition.

Preferably, when the composition is in liquid form, it comprises at least one additional filler, preferably chosen from kaolin, bentone, lauroyllysine and starch.

Agent for Structuring the Fatty Phase

The structuring agent is chosen from structuring polymers and lipophilic gelling agents, i.e. oil-gelling agents, also known as "organogelling agents", and mixtures thereof.

The fatty phase may also comprise several structuring agents chosen from structuring polymers and lipophilic gelling agents; this will then be referred to as a "structuring system".

Non-Polymeric Organogelling Agent

The composition according to the invention may contain one or more specific organogelling agents.

According to the invention, an "organogelling agent" is defined as comprising an organic compound whose molecules may be capable of establishing, between themselves, at least one physical interaction leading to self-aggregation of the molecules with formation of a three-dimensional macromolecular network that may be responsible for the gelation of the liquid fatty phase. The network may result from the formation of a network of fibrils (caused by the stacking or aggregation of organogelling molecules), which immobilizes the molecules of the liquid fatty phase. Depending on the nature of the organogelling agent, the interconnected fibrils have variable sizes that may range from a few nanometres up to 1 µm or even several micrometers. These fibrils may occasionally combine to form strips or columns.

The term "gelation" means structuring or, more generally, thickening of the medium, which may lead according to the invention to a fluid to pasty or even solid consistency.

The ability to form this network of fibrils, and thus to gel the composition, depends on the nature (or chemical class) of the organogelling agent, on the nature of the substituents borne by its molecules for a given chemical class, and on the nature of the liquid fatty phase.

For example, this gelation is reversible under the action of an external stimulus such as the temperature.

The physical interactions are of diverse nature but may include co-crystallization. These physical interactions are, for example, interactions chosen from self-complementary hydrogen interactions, $\pi$ interactions between unsaturated nuclei, dipolar interactions, and coordination bonds with organometallic derivatives. The establishment of these interactions may often be promoted by the architecture of the molecule, for example by nuclei, unsaturations and the presence of asymmetric carbon. In general, each molecule of an organogelling agent can establish several types of physical interaction with a neighboring molecule. Thus, in one embodiment, the molecules of the organic gelling agent according to the invention may comprise at least one group that is capable of establishing hydrogen bonds, for example at least two groups that are capable of establishing hydrogen bonds; at least one aromatic nucleus, for example at least two aromatic nuclei; at least one bond with ethylenic unsaturation; and/or at least one asymmetric carbon. The groups that are capable of forming a hydrogen bond may be chosen, for example, from hydroxyl, carbonyl, amine, carboxylic acid, amide, benzyl, sulfonamide, carbamate, thiocarbamate, urea, thiourea, oxamido, guanidino and biguanidino groups.

The organogelling agents of the invention may be solid or liquid at room temperature (20° C.) and at atmospheric pressure.

Among the lipophilic gelling agents that may be mentioned are combinations of at least one low molecular weight dialkyl N-acylglutamide bearing a linear alkyl chain, chosen especially from ($C_2$-$C_6$)dialkyl N-acylglutamides in which the acyl group comprises a linear $C_8$ to $C_{22}$ alkyl chain such as lauroylglutamic acid dibutylamide (or dibutyl lauroyl glutamide), with at least one low molecular weight dialkyl N-acylglutamide bearing a branched alkyl chain, chosen especially from ($C_2$-$C_6$)dialkyl N-acylglutamides in which the acyl group comprises a branched $C_8$ to $C_{22}$ alkyl chain such as N-2-ethylhexanoyl glutamic acid dibutylamide (or dibutyl ethylhexanoyl glutamide) and preferably with a solvent that is capable of forming hydrogen bonds with these two low molecular weight lipophilic gelling agents.

Preferably, the dialkyl N-acylglutamide with a linear alkyl chain is used in a content ranging from 0.1% to 10%, preferably 0.5% to 5% and more preferably 1.0% to 3.0% by weight relative to the total weight of the fatty phase.

Preferably, the dialkyl N-acylglutamide with a branched alkyl chain is used in an amount ranging from 0.1% to 10%, preferably 0.5% to 5% and more preferably 1.0% to 3.0% by weight relative to the total weight of the fatty phase.

More preferably, the total amount of lipophilic gelling agents of low molecular weight N-acylglutamic acid diamide type is preferably less than or equal to 7% by weight relative to the total weight of the fatty phase.

Lauroylglutamic acid dibutylamide is sold or manufactured by the company Ajinomoto under the name GP-1, of INCI name: Dibutyl Lauroyl Glutamide, and N-2-ethylhexanoylglutamic acid dibutylamide is sold or manufactured by the company Ajinomoto under the name EB-21, of INCI name: Dibutyl Ethylhexanoyl Glutamide. Such a compound is described in patent application JP2005-298635.

According to a preferred variant, the ratio of the low molecular weight linear-chain N-acylglutamic acid diamides/low molecular weight branched-chain N-acylglutamic acid diamide is between 1/1 and 5/1, preferably between 1.5/1 and 3/1 and preferably between 1.7/1 and 2/1.

The solvent that is capable of forming hydrogen bonds with the lipophilic gelling agents is a protic solvent preferentially chosen, for example, from alcohols, especially monoalcohols comprising more than 8 carbon atoms, dialcohols, acids and esters.

Preferably, the solvent that is capable of forming hydrogen bonds between the lipophilic gelling agents is chosen from $C_2$-$C_5$ glycols such as propylene glycol, butylene glycols and pentene glycols. This solvent may also be chosen from octyldodecanol and isostearyl alcohol. The amount of solvents capable of forming hydrogen bonds ranges from 3% to 50% by weight, preferably between 5% and 40% and more preferably from 7% to 20% by weight relative to the total weight of the base.

Preferentially, the solvent is a fatty alcohol, particularly chosen from fatty alcohols with a fatty chain length of between 12 and 28 carbon atoms, preferentially between 14 and 22 and better still between 16 and 20 carbon atoms.

Even more particularly, the solvent is a branched fatty-chain alcohol.

Structuring Polymers

As structuring polymers, besides the indene hydrocarbon-based resins and the block copolymers comprising at least one styrene monomer, mention may be made of hydrocarbon-based polyamides, silicone polyamides, the polyurethanes of INCI name Dilinoleyl Dimer Diol-Based Polyurethane, or mixtures thereof.

Polyamides

According to a preferred embodiment, the composition according to the invention comprises at least one polyamide chosen from hydrocarbon-based polyamides and silicone polyamides, and mixtures thereof.

Preferably, the total content of polyamide(s) is between 0.1% and 30% by weight, preferably between 0.1% and 20% by weight and preferably between 0.5% and 10% by weight relative to the total weight of the composition.

For the purposes of the invention, the term "polymer" means a compound containing at least two repeating units, preferably at least three repeating units and better still ten repeating units.

For the purposes of the invention, the term "polyamide" means a compound containing at least two repeating amide units, preferably at least three repeating amide units and better still ten repeating amide units.

Hydrocarbon-Based Polyamide

The term "hydrocarbon-based polyamide" means a polyamide formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

For the purposes of the invention, the term "functionalized chains" means an alkyl chain comprising one or more functional groups or reagents chosen especially from hydroxyl, ether, esters, oxyalkylene and polyoxyalkylene groups.

Advantageously, this polyamide of the composition according to the invention has a weight-average molecular mass of less than 100 000 g/mol (especially ranging from 1000 to 100 000 g/mol), in particular less than 50 000 g/mol (especially ranging from 1000 to 50 000 g/mol) and more particularly ranging from 1000 to 30 000 g/mol, preferably from 2000 to 20 000 g/mol and better still from 2000 to 10 000 g/mol.

This polyamide is insoluble in water, especially at 25° C.

According to a first embodiment of the invention, the polyamide used is a polyamide of formula (I):

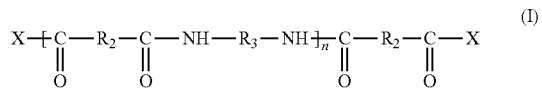

(I)

in which X represents a group —N(R$_1$)$_2$ or a group —OR$_1$ in which R$_1$ is a linear or branched C$_8$ to C$_{22}$ alkyl radical which may be identical or different, R$_2$ is a C$_{28}$-C$_{42}$ diacid dimer residue, R$_3$ is an ethylenediamine radical and n is between 2 and 5;

and mixtures thereof.

According to a particular mode, the polyamide used is an amide-terminated polyamide of formula (Ia)

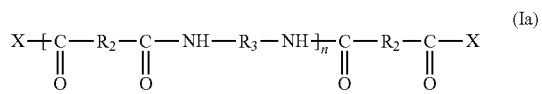

(Ia)

in which X represents a group —N(R$_1$)$_2$ in which R$_1$ is a linear or branched C$_8$ to C$_{22}$ alkyl radical which may be identical or different, R$_2$ is a C$_{28}$-C$_{42}$ diacid dimer residue, R$_3$ is an ethylenediamine radical and n is between 2 and 5;
and mixtures thereof;

The composition may also comprise, additionally in this case, at least one additional polyamide of formula (Ib)

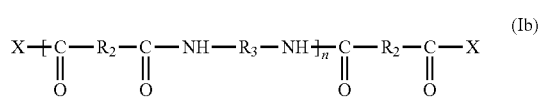

(Ib)

in which X represents a group —OR$_1$ in which R$_1$ is a linear or branched C$_8$ to C$_{22}$ and preferably C$_{16}$ to C$_{22}$ alkyl radical which may be identical or different, R$_2$ is a C$_{28}$-C$_{42}$ diacid dimer residue, R$_3$ is an ethylenediamine radical and n is between 2 and 5.

As polyamide compounds of formula (Ib)

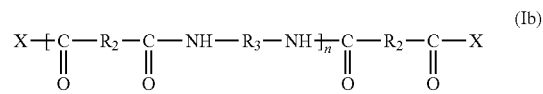

(Ib)

in which X represents a group —OR$_1$ in which R$_1$ is a linear or branched C$_8$ to C$_{22}$ and preferably C$_{16}$ to C$_{22}$ alkyl radical which may be identical or different, R$_2$ is a C$_{28}$-C$_{42}$ diacid dimer residue, R$_3$ is an ethylenediamine radical and n is between 2 and 5, mention may be made of the commercial products sold by the company Arizona Chemical under the names Uniclear 80 and Uniclear 100 or Uniclear 80 V, Uniclear 100 V and Uniclear 100 VG, the INCI name of which is Ethylenediamine/stearyl dimer dilinoleate copolymer. They are sold, respectively, in the form of a gel containing 80% active material in a mineral oil and at 100% active material. They have a softening point of from 88 to 94° C. These commercial products are a mixture of copolymers of a C$_{36}$ diacid coupled with ethylenediamine, having a weight-average molecular mass of about 6000 g/mol. The terminal ester groups result from the esterification of the remaining acid end groups with cetyl alcohol, stearyl alcohol or mixtures thereof (also known as cetylstearyl alcohol).

As amide-terminated polyamide compounds such as those described in patent application US 2009/0 280 076, and in particular an amide-terminated polyamide of formula (Ia)

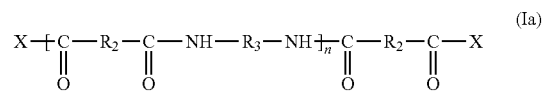

(Ia)

in which X represents a group —N(R$_1$)$_2$ in which R$_1$ is a linear or branched C$_8$ to C$_{22}$, preferably C$_8$ to C$_{20}$, preferably C$_{14}$ to C$_{20}$ and more preferentially C$_{14}$ to C$_{18}$ and better still C$_{18}$ alkyl radical, which may be identical or different, R$_2$ is a C$_{28}$-C$_{42}$ diacid dimer residue, preferably a dilinoleic acid dimer residue, R$_3$ is an ethylenediamine radical, and n is between 2 and 5 and preferably between 3 and 4, mention may be made of the compound of formula (Ia) whose INCI name is bis-dioctadecylamide dimer dilinoleic acid/ethylenediamine copolymer.

As a specific example of an amide-terminated polyamide that may be used, mention may be made of the compound Haimalate PAM sold by the company Kokyu Alcohol Kogyo, which is in combination with diisostearyl malate and whose INCI name is diisostearyl malate (and) bis-dioctadecylamide dimer dilinoleic acid/ethylenediamine copolymer.

According to another embodiment of the invention, the polyamide is a silicone polyamide.

Silicone Polyamide

The silicone polyamides of the composition are preferably solid at room temperature (25° C.) and atmospheric pressure (760 mmHg).

The silicone polyamides may be more particularly polymers comprising at least one unit of formula (III) or (IV):

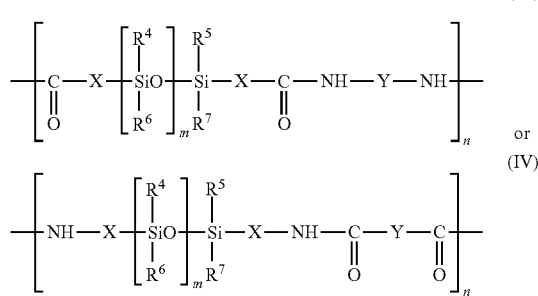

in which:
R$^4$, R$^5$, R$^6$ and R$^7$, which may be identical or different, represent a group chosen from:
linear, branched or cyclic, saturated or unsaturated, C$_1$ to C$_{40}$ hydrocarbon-based groups, possibly containing in their chain one or more oxygen, sulfur and/or nitrogen atoms, and possibly being partially or totally substituted with fluorine atoms,
C$_6$-C$_{10}$ aryl groups, optionally substituted with one or more C$_1$-C$_4$ alkyl groups,
polyorganosiloxane chains possibly containing one or more oxygen, sulfur and/or nitrogen atoms,
   the groups X, which may be identical or different, represent a linear or branched C$_1$ to C$_{30}$ alkylenediyl group, possibly containing in its chain one or more oxygen and/or nitrogen atoms;
   Y is a saturated or unsaturated C$_1$ to C$_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, C$_3$ to C$_8$ cycloalkyl, C$_1$ to C$_{40}$ alkyl, C$_5$ to C$_{10}$ aryl, phenyl optionally substituted with one to three C$_1$ to C$_3$ alkyl, C$_1$ to C$_3$ hydroxyalkyl and C$_1$ to C$_6$ aminoalkyl groups, or
Y represents a group corresponding to the formula:

in which:
T represents a linear or branched, saturated or unsaturated, C$_3$ to C$_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
R$^8$ represents a linear or branched C$_1$-C$_{50}$ alkyl group or a polyorganosiloxane chain, possibly comprising one or more ester, amide, urethane, thiocarbamate, urea, thiourea and/or sulfonamide groups, which may possibly be linked to another chain of the polymer;
n is an integer ranging from 2 to 500 and preferably from 2 to 200, and m is an integer ranging from 1 to 1000, preferably from 1 to 700 and better still from 6 to 200.

According to an embodiment of the invention, 80% of the groups R$^4$, R$^5$, R$^6$ and R$^7$ of the polymer are preferably chosen from methyl, ethyl, phenyl and 3,3,3-trifluoropropyl groups. According to another embodiment, 80% of the groups R$^4$, R$^5$, R$^6$ and R$^7$ of the polymer are methyl groups.

According to the invention, Y can represent various divalent groups, furthermore optionally comprising one or two free valencies to establish bonds with other units of the polymer or copolymer. Preferably, Y represents a group chosen from:
a) linear C$_1$ to C$_{20}$ and preferably C$_1$ to C$_{10}$ alkylene groups,
b) C$_{30}$ to C$_{50}$ branched alkylene groups possibly comprising rings and unconjugated unsaturations,
c) C$_5$-C$_6$ cycloalkylene groups,
d) phenylene groups optionally substituted with one or more C$_1$ to C$_{40}$ alkyl groups,
e) C$_1$ to C$_{20}$ alkylene groups comprising from 1 to 5 amide groups,
f) C$_1$ to C$_{20}$ alkylene groups comprising one or more substituents chosen from hydroxyl, C$_3$ to C$_8$ cycloalkane, C$_1$ to C$_3$ hydroxyalkyl and C$_1$ to C$_6$ aminoalkyl groups,
g) polyorganosiloxane chains of formula:

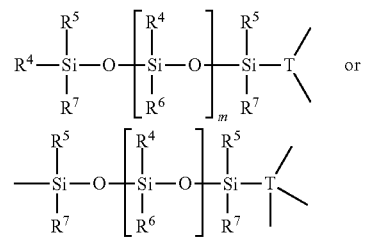

in which R$^4$, R$^5$, R$^6$, R$^7$, T and m are as defined above.
Such a unit may be obtained:
either by a condensation reaction between a silicone containing α,ω-carboxylic acid ends and one or more diamines, according to the following reaction scheme:

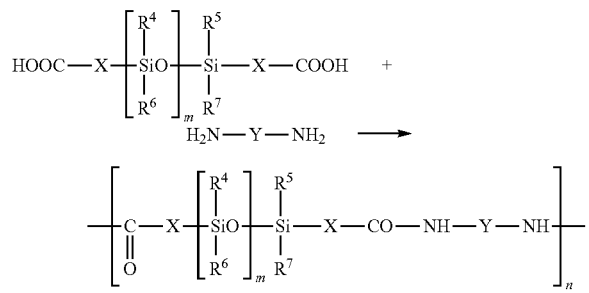

or by reaction of two molecules of α-unsaturated carboxylic acid with a diamine according to the following reaction scheme:

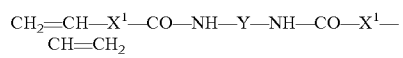

followed by the addition of a siloxane to the ethylenic unsaturations, according to the following scheme:

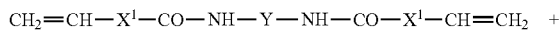

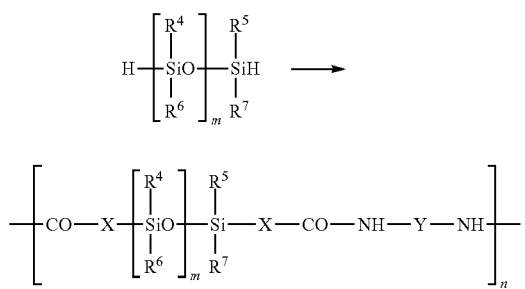

in which X¹—(CH$_2$)$_2$— corresponds to X defined above and Y, R$^4$, R$^5$, R$^6$, R$^7$ and m are as defined above;

or by reaction of a silicone containing α,ω-NH$_2$ ends and a diacid of formula HOOC—Y—COOH according to the following reaction scheme:

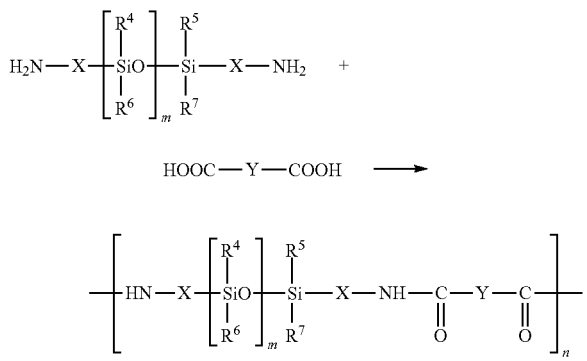

In these silicone polyamides of formula (III) or (IV), m is in the range from 1 to 700, in particular from 15 to 500 and especially from 50 to 200, and n is in particular in the range from 1 to 500, preferably from 1 to 100 and better still from 4 to 25, X is preferably a linear or branched alkylene chain containing from 1 to 30 carbon atoms, in particular 1 to 20 carbon atoms, especially from 5 to 15 carbon atoms and more particularly 10 carbon atoms, and Y is preferably an alkylene chain that is linear or branched, or which may comprise rings and/or unsaturations, containing from 1 to 40 carbon atoms, in particular 1 to 20 carbon atoms and better still from 2 to 6 carbon atoms, in particular 6 carbon atoms.

In formulae (III) and (IV), the alkylene group representing X or Y can optionally contain in its alkylene portion at least one of the following members:

1 to 5 amide, urea, urethane or carbamate groups, a C$_5$ or C$_6$ cycloalkyl group, and a phenylene group optionally substituted with 1 to 3 identical or different C$_1$ to C$_3$ alkyl groups.

In formulae (III) and (IV), the alkylene groups may also be substituted with at least one component chosen from the group consisting of:

a hydroxyl group, a C$_3$ to C$_8$ cycloalkyl group, one to three C$_1$ to C$_{40}$ alkyl groups, a phenyl group optionally substituted with one to three C$_1$ to C$_3$ alkyl groups, a C$_1$ to C$_3$ hydroxyalkyl group, and a C$_1$ to C$_6$ aminoalkyl group.

In these formulae (III) and (IV), Y may also represent:

in which R$^8$ represents a polyorganosiloxane chain and T represents a group of formula:

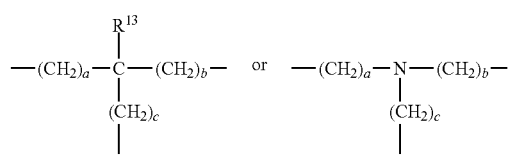

in which a, b and c are, independently, integers ranging from 1 to 10, and R$^{13}$ is a hydrogen atom or a group such as those defined for R$^4$, R$^5$, R$^6$ and R$^7$.

In formulae (III) and (IV), R$^4$, R$^5$, R$^6$ and R$^7$ preferably represent, independently, a linear or branched C$_1$ to C$_{40}$ alkyl group, preferably a CH$_3$, C$_2$H$_5$, n-C$_3$H$_7$ or isopropyl group, a polyorganosiloxane chain or a phenyl group optionally substituted with one to three methyl or ethyl groups.

As has been seen previously, the polymer may comprise identical or different units of formula (III) or (IV).

Thus, the polymer may be a polyamide containing several units of formula (III) or (IV) of different lengths, i.e. a polyamide corresponding to formula (V):

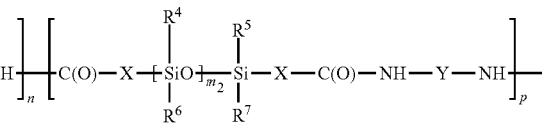

in which X, Y, n and R$^4$ to R$^7$ have the meanings given above, m$_1$ and m$_2$, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the polymer may correspond to formula VI:

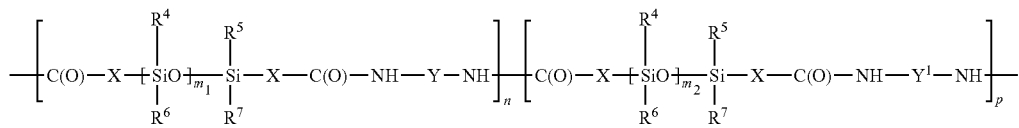

in which $R^4$ to $R^7$, X, Y, $m_1$, $m_2$, n and p have the meanings given above and $Y^1$ is different than Y but chosen from the groups defined for Y. As previously, the various units may be structured to form either a block copolymer, or a random copolymer or an alternating copolymer.

In this first embodiment of the invention, the silicone polyamide may also consist of a grafted copolymer. Thus, the polyamide containing silicone units may be grafted and optionally crosslinked with silicone chains containing amide groups. Such polymers may be synthesized with trifunctional amines. In this case, the polymer may comprise at least one unit of formula (VII):

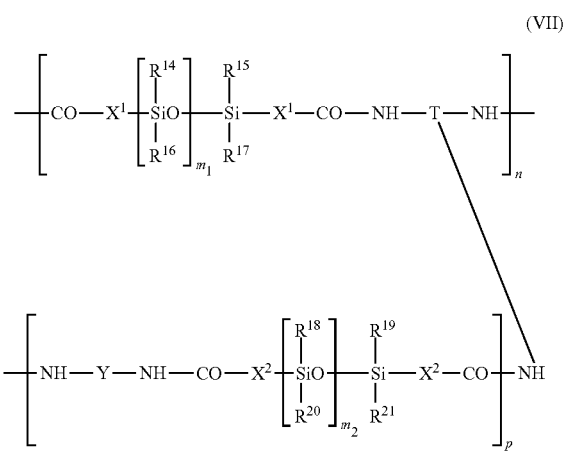

(VII)

in which $X^1$ and $X^2$, which are identical or different, have the meaning given for X in formula (III), n is as defined in formula (III), Y and T are as defined in formula (III), $R^{14}$ to $R^{21}$ are groups chosen from the same group as $R^4$ to $R^7$, $m_1$ and $m_2$ are numbers in the range from 1 to 1000, and p is an integer ranging from 2 to 500.

In formula (VII), it is preferred that:
p is in the range from 1 to 25 and better still from 1 to 7,
$R^{14}$ to $R^{21}$ are methyl groups,
T corresponds to one of the following formulae:

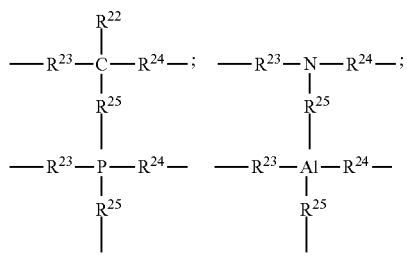

in which $R^{22}$ is a hydrogen atom or a group chosen from the groups defined for $R^4$ to $R^7$, and $R^{23}$, $R^{24}$ and $R^{25}$ are, independently, linear or branched alkylene groups, and more preferably correspond to the formula:

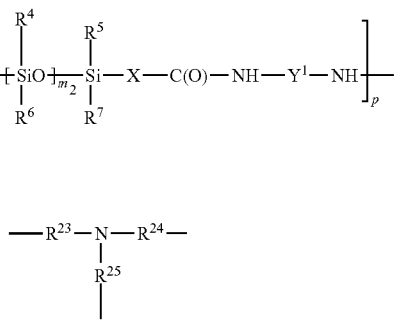

in particular with $R^{23}$, $R^{24}$ and $R^{25}$ representing —$CH_2$—$CH_2$—, $m_1$ and $m_2$ are in the range from 15 to 500 and better still from 15 to 45, X1 and X2 represent —$(CH_2)_{10}$—, and Y represents —$CH_2$—.

As has been seen previously, the siloxane units may be in the main chain or backbone of the polymer, but they may also be present in grafted or pendent chains. In the main chain, the siloxane units may be in the form of segments as described above. In the side or grafted chains, the siloxane units may appear individually or in segments.

According to one preferred embodiment variant of the invention, a copolymer comprising units of formula (III) or (IV) and hydrocarbon-based polyamide units may be used. In this case, the polyamide-silicone units may be located at the ends of the hydrocarbon-based polyamide.

According to a preferred embodiment, the silicone polyamide comprises units of formula III.

Preferably, according to this embodiment, the groups $R^4$, $R^5$, $R^6$ and $R^7$ represent methyl groups, one from among X and Y represents an alkylene group containing 6 carbon atoms and the other represents an alkylene group containing 11 carbon atoms.

n is an integer ranging from 2 to 500, and n represents the degree of polymerization DP of the polymer.

As examples of such silicone polyamides, mention may be made of the compounds sold by the company Dow Corning under the names DC2-8179 (DP 100) and DC2-8178 (DP 15), the INCI name of which is Nylon-611/dimethicone copolymers.

Advantageously, the composition used according to the invention comprises at least one polydimethylsiloxane block polymer of general formula (I) with an m value of about 100.

The "m" valve corresponds to the degree of polymerization of the silicone part of the polymer.

More preferably, the composition used according to the invention comprises at least one polymer comprising at least one unit of formula (III) in which m ranges from 50 to 200, in particular from 75 to 150 and is preferably about 100.

More preferably, $R^4$, $R^5$, $R^6$ and $R^7$ independently represent a linear or branched $C_1$ to $C_{40}$ alkyl group, preferably a group $CH_3$, $C_2H_5$, n-$C_3H_7$ or isopropyl in formula (III).

As examples of silicone polymers that may be used, mention may be made of one of the silicone polyamides obtained in accordance with Examples 1 to 3 of document U.S. Pat. No. 5,981,680.

According to a preferred mode, use is made of the silicone polyamide polymer sold by the company Dow Corning under the name DC2-8179 (DP 100).

The silicone polymers and/or copolymers used in the composition of the invention advantageously have a temperature of transition from the solid state to the liquid state ranging from 45° C. to 190° C. Preferably, they have a temperature of transition from the solid state to the liquid state ranging from 70° C. to 130° C. and better still from 80° C. to 105° C.

Preferably, the total amount of structuring polymers as defined previously present in the compositions used according to the invention is between 0.1% and 40% by weight, or between 0.2% and 25% by weight, or better still between 0.2% and 20% by weight of active material relative to the total weight of the composition (limits inclusive).

Advantageously, the total amount of structuring polymers as defined previously (structuring polymers and organogelling agents) present in the compositions used according to the invention is between 0.1% and 40% by weight, or between 0.2% and 25% by weight, or better still between 0.2% and 20% by weight of active material relative to the total weight of the composition (limits inclusive).

According to a preferred embodiment, the composition according to the invention comprises a polyamide chosen from:
(i) polyamide of formula (Ib)

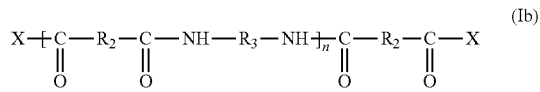

(Ib)

in which X represents a group —OR$_1$ in which R$_1$ is a linear or branched C$_8$ to C$_{22}$ and preferably C$_{16}$ to C$_{22}$ alkyl radical which may be identical or different, R$_2$ is a C$_{28}$-C$_{42}$ diacid dimer residue, R$_3$ is an ethylenediamine radical and n is between 2 and 5, and/or
(ii) a hydrocarbon-based polyamide bearing an amide end group of formula (Ia), and/or
(iii) a silicone polyamide of formula (III) or (IV), and/or
(iv) mixtures thereof.

According to one embodiment, preferably when the polyamide is a hydrocarbon-based polyamide, the composition according to the invention may also comprise a mixture
of a (C$_2$-C$_6$)dialkyl N-acylglutamide in which the acyl group comprises a linear C$_8$ to C$_{22}$ alkyl chain, preferably N-lauroylglutamic acid dibutylamide, and
of a (C$_2$-C$_6$)dialkyl N-acylglutamide in which the acyl group comprises a branched C$_8$ to C$_{22}$ alkyl chain, preferably N-2-ethylhexanoylglutamic acid dibutylamide.

According to one preferred embodiment, the structuring system comprises an ester-terminated polyamide, preferably the compound whose INCI name is Ethylenediamine/stearyl dimer dilinoleate copolymer sold by the company Arizona Chemical under the name Uniclear 100 VG, and optionally a mixture of N-lauroylglutamic acid dibutylamide and of N-2-ethylhexanoylglutamic acid dibutylamide.

Semi-Crystalline Polymer

The composition according to the invention may also advantageously comprise at least one semi-crystalline polymer. Preferably, the semi-crystalline polymer has an organic structure, and a melting point of greater than or equal to 30° C.

Preferably, the total amount of semi-crystalline polymer(s) represents from 0.1% to 30% and better still from 0.1% to 20% by weight relative to the total weight of the composition. Preferably, the total amount of semi-crystalline polymer(s) represents from 0.3% to 10% of the total weight of the composition.

For the purposes of the invention, the term "polymers" means compounds comprising at least two repeating units, preferably at least three repeating units and more especially at least ten repeating units.

For the purposes of the invention, the term "semi-crystalline polymer" means polymers comprising a crystallizable portion and an amorphous portion and having a first-order reversible change of phase temperature, in particular of melting (solid-liquid transition). The crystallizable portion is either a side chain (or pendent chain) or a block in the backbone.

When the crystallizable portion of the semi-crystalline polymer is a block of the polymer backbone, this crystallizable block has a chemical nature different from that of the amorphous blocks; in this case, the semi-crystalline polymer is a block copolymer, for example of the diblock, triblock or multiblock type. When the crystallizable portion is a chain that is pendent on the backbone, the semi-crystalline polymer may be a homopolymer or a copolymer.

The terms "organic compound" and "having an organic structure" mean compounds containing carbon atoms and hydrogen atoms and optionally heteroatoms such as S, O, N or P, alone or in combination.

The melting point of the semi-crystalline polymer is preferably less than 150° C.

The melting point of the semi-crystalline polymer is preferably greater than or equal to 30° C. and less than 100° C. More preferably, the melting point of the semi-crystalline polymer is preferably greater than or equal to 30° C. and less than 70° C.

The semi-crystalline polymer(s) according to the invention are solid at room temperature (25° C.) and atmospheric pressure (760 mmHg), with a melting point of greater than or equal to 30° C. The melting point values correspond to the melting point measured using a differential scanning calorimeter (DSC), such as the calorimeter sold under the name DSC 30 by the company Mettler, with a temperature rise of 5° C. or 10° C. per minute. (The melting point under consideration is the point corresponding to the temperature of the most endothermic peak of the thermogram).

The semi-crystalline polymer(s) according to the invention preferably have a melting point that is higher than the temperature of the keratinous support intended to receive the said composition, in particular the skin or the lips.

According to the invention, the semi-crystalline polymers are advantageously soluble in the fatty phase, especially to at least 1% by weight, at a temperature that is higher than their melting point. Apart from the crystallizable chains or blocks, the blocks of the polymers are amorphous.

Within the meaning of the invention, the expression "crystallizable chain or block" is understood to mean a chain or block which, if it were alone, would change from the amorphous state to the crystalline state reversibly, according to whether the temperature is above or below the melting point. Within the meaning of the invention, a "chain" is a group of atoms, which is pendent or lateral with respect to the backbone of the polymer. A block is a group of atoms belonging to the backbone, this group constituting one of the repeat units of the polymer.

Preferably, the polymer backbone of the semi-crystalline polymers is soluble in the fatty phase at a temperature above their melting point.

Preferably, the crystallizable blocks or chains of the semi-crystalline polymers represent at least 30% of the total weight of each polymer and better still at least 40%. The semi-crystalline polymers containing crystallizable side chains are homopolymers or copolymers. The semi-crystalline polymers of the invention containing crystallizable blocks are block or multiblock copolymers. They may be obtained via polymerization of a monomer containing reactive double bonds (or ethylenic bonds) or via polycondensation. When the polymers of the invention are polymers having crystallizable side chains, these side chains are advantageously in random or statistical form.

Preferably, the semi-crystalline polymers of the invention are of synthetic origin.

According to one preferred embodiment, the semi-crystalline polymer is chosen from:
  homopolymers and copolymers comprising units resulting from the polymerization of one or more monomers bearing crystallizable hydrophobic side chain(s),
  polymers bearing in the backbone at least one crystallizable block,
  polycondensates of aliphatic or aromatic or aliphatic/aromatic polyester type,
  copolymers of ethylene and propylene prepared via metallocene catalysis.

The semi-crystalline polymers that may be used in the invention may in particular be chosen from:
  block copolymers of polyolefins of controlled crystallization, whose monomers are described in EP-A-0 951 897,
  polycondensates, especially of aliphatic or aromatic or aliphatic/aromatic polyester type,
  copolymers of ethylene and propylene prepared via metallocene catalysis,
  homopolymers or copolymers bearing at least one crystallizable side chain and homopolymers or copolymers bearing at least one crystallizable block in the backbone, for instance those described in document U.S. Pat. No. 5,156,911,
  homopolymers or copolymers bearing at least one crystallizable side chain, in particular bearing fluoro group(s), such as those described in document WO-A-01/19333,
  and mixtures thereof.

In the last two cases, the crystallizable side chain(s) or block(s) are hydrophobic.

A) Semi-Crystalline Polymers Containing Crystallizable Side Chains

The polymers and copolymers are particularly preferably chosen from semi-crystalline polymers bearing crystallizable side chains.

Mention may be made in particular of those defined in documents U.S. Pat. No. 5,156,911 and WO-A-01/19333.

They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned hereinbelow with, in particular, the characteristic of being soluble or dispersible in the fatty phase, by heating above their melting point mp. They can result:
  from the polymerization, in particular radical polymerization, of one or more monomers having reactive ethylenic double bond(s) with respect to a polymerization, namely having a vinyl, (meth)acrylic or allylic group,
  from the polycondensation of one or more monomers bearing co-reactive groups (carboxylic acid, sulfonic acid, alcohol, amine or isocyanate), for instance polyesters, polyurethanes, polyethers or polyureas.

a) In general, the crystallizable units (chains or blocks) of the semi-crystalline polymers according to the invention are derived from monomer(s) containing crystallizable block(s) or chain(s), used for manufacturing semi-crystalline polymers. These polymers are preferably chosen especially from homopolymers and copolymers resulting from the polymerization of at least one monomer containing crystallizable chain(s) that may be represented by formula X:

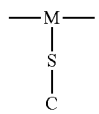

with M representing an atom of the polymer backbone, C representing a crystallizable group and S representing a spacer. The "—S—C" crystallizable chains are optionally fluorinated or perfluorinated, hydrocarbon-based aliphatic or aromatic chains, comprising saturated or unsaturated $C_{12}$-$C_{40}$, preferably $C_{12}$-$C_{28}$ and preferably $C_{14}$-$C_{24}$ hydrocarbon-based alkyl chains.

"C" especially represents a group $(CH_2)_n$, which may be linear or branched or cyclic, with n being an integer ranging from 12 to 40. Preferably, "C" is a linear group. Preferably, "S" and "C" are different.

When the crystallizable chains are hydrocarbon-based aliphatic chains, they comprise hydrocarbon-based alkyl chains containing at least 12 carbon atoms and not more than 40 carbon atoms and better still not more than 24 carbon atoms. They are especially aliphatic chains or alkyl chains containing at least 12 carbon atoms, and they are preferably $C_{12}$-$C_{40}$, preferably $C_{12}$-$C_{28}$, preferably $C_{14}$-$C_{24}$ and preferably $C_{16}$-$C_{22}$ alkyl chains.

Preferably, the crystallizable chains are $C_{16}$-$C_{22}$ hydrocarbon-based aliphatic chains.

When they are fluoroalkyl or perfluoroalkyl chains, they comprise at least 11 carbon atoms, at least 6 of which carbon atoms are fluorinated.

As examples of semi-crystalline homopolymers or copolymers bearing crystallizable chain(s), mention may be made of those resulting from the polymerization of one or more of the following monomers: (meth)acrylates of saturated alkyl with the alkyl group being $C_{14}$-$C_{24}$, perfluoroalkyl (meth)acrylates with a $C_{11}$-$C_{15}$ perfluoroalkyl group, N-alkyl(meth)acrylamides with the alkyl group being $C_{14}$ to $C_{24}$ with or without a fluorine atom, vinyl esters containing alkyl or perfluoro(alkyl) chains with the alkyl group being $C_{14}$ to $C_{24}$ (with at least 6 fluorine atoms per perfluoroalkyl chain), vinyl ethers containing alkyl or perfluoro(alkyl) chains with the alkyl group being $C_{14}$ to $C_{24}$ and at least 6 fluorine atoms per perfluoroalkyl chain, $C_{14}$ to $C_{24}$ α-olefins such as, for example, octadecene, para-alkylstyrenes with an alkyl group containing from 12 to 24 carbon atoms, and mixtures thereof.

When the polymers result from a polycondensation, the crystallizable hydrocarbon-based and/or fluorinated chains as defined above are carried by a monomer which can be a diacid, a diol, a diamine or a diisocyanate.

When the polymers that are the subject of the invention are copolymers, they additionally contain from 0 to 50% of groups Y which is a polar or non-polar monomer or a mixture of the two.

When Y is a polar monomer, it is either a monomer bearing polyoxyalkylenated groups (especially oxyethylenated and/or oxypropylenated groups), a hydroxyalkyl (meth)acrylate, for instance hydroxyethyl acrylate, (meth) acrylamide, an N-alkyl(meth)acrylamide, an N,N-dialkyl (meth)acrylamide such as, for example, N,N-diisopropylacrylamide or N-vinylpyrrolidone (NVP), N-vinylcaprolactam, a monomer bearing at least one carboxylic acid group, for instance (meth)acrylic acid, crotonic acid, itaconic acid, maleic acid or fumaric acid, or bearing a carboxylic acid anhydride group, for instance maleic anhydride, and mixtures thereof.

When Y is a non-polar monomer, it may be an ester of the linear, branched or cyclic alkyl (meth)acrylate type, a vinyl ester, an alkyl vinyl ether, an α-olefin, styrene or styrene substituted with a $C_1$ to $C_{10}$ alkyl group, for instance α-methylstyrene, or a macromonomer of the polyorganosiloxane type containing vinyl unsaturation.

For the purposes of the invention, the term "alkyl" means a saturated group especially of $C_8$ to $C_{24}$, except where otherwise mentioned.

Preferably, the semicrystalline polymers having a crystallizable side chain are alkyl (meth)acrylate or alkyl(meth) acrylamide homopolymers with an alkyl group as defined above, in particular a $C_{14}$-$C_{24}$ alkyl group, copolymers of these monomers with a hydrophilic monomer preferably different in nature from (meth)acrylic acid, such as N-vinylpyrrolidone or hydroxyethyl (meth)acrylate, and mixtures thereof.

Advantageously, the semi-crystalline polymer(s) containing a crystallizable side chain has (have) a weight-average molecular mass Mp ranging from 5000 to 1 000 000, preferably from 10 000 to 800 000, preferentially from 15 000 to 500 000 and more preferably from 100 000 to 200 000.

In particular, the semi-crystalline polymers bearing crystallizable side chain(s) are alkyl (meth)acrylate homopolymers or copolymers with an alkyl group as defined above, and mixtures thereof.

According to one particular embodiment of the invention, a polymer may be chosen from homopolymers and copolymers resulting from the polymerization of at least one monomer with a crystallizable side chain chosen from saturated $C_{10}$ to $C_{30}$ alkyl (meth)acrylates, which may be represented by the formula below:

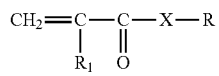

in which $R_1$ is H or $CH_3$, R represents a $C_{10}$ to $C_{30}$ alkyl group and X represents O.

According to a more particular embodiment of the invention, the polymer is derived from the polymerization of monomers bearing a crystallizable chain, chosen from saturated $C_{10}$ to $C_{30}$ alkyl (meth)acrylates.

As a particular example of a semi-crystalline polymer that may be used in the composition according to the invention, mention may be made of the Intelimer® products from the company Landec described in the brochure "Intelimer® polymers", Landec IP22 (Rev. 4-97). These polymers are in solid form at room temperature (25° C.). They bear crystallizable side chains and have the formula X above. They are poly($C_{10}$-$C_{30}$)alkyl acrylates, which are particularly suitable as semi-crystalline polymers that may be included in a composition in accordance with the present invention.

The semi-crystalline polymers that may be used in the invention are in particular homopolymers or copolymers bearing at least one crystallizable side chain, such as those described in document U.S. Pat. No. 5,156,911, and mixtures thereof.

These polymers may especially have a molecular weight ranging from 15 000 to 500 000 and preferably from 100 000 to 200 000.

For example, the product Intelimer® IPA 13-1 from the company Landec is chosen, which is a polystearyl acrylate with a molecular weight of about 145 000 and a melting point of 49° C.

They are homopolymers or copolymers comprising from 50% to 100% by weight of units resulting from the polymerization of one or more monomers carrying a crystallizable hydrophobic side chain.

These homopolymers or copolymers are of any nature, provided that they meet the conditions mentioned hereinbelow with, in particular, the characteristic of being soluble or dispersible in the liquid fatty phase, by heating above their melting point. They may result from the polymerization, especially the free-radical polymerization, of one or more monomers containing reactive or ethylenic double bond(s) with respect to a polymerization, namely a vinyl, (meth) acrylic or allylic group.

The semi-crystalline polymers bearing a crystallizable side chain may be chosen from copolymers resulting from the copolymerization of acrylic acid and of a $C_{10}$ to $C_{16}$ alkyl (meth)acrylate, especially such as those described in Examples 3, 4 and 9 of U.S. Pat. No. 5,156,911

The semi-crystalline polymers may especially be those described in Examples 3, 4, 5, 7 and 9 of U.S. Pat. No. 5,156,911, and more particularly from the copolymerization:
 of acrylic acid, of hexadecyl acrylate and of isodecyl acrylate in a 1/16/3 ratio,
 of acrylic acid and of pentadecyl acrylate in a 1/19 ratio,
 of acrylic acid, of hexadecyl acrylate and of ethyl acrylate in a 2.5/76.5/20 ratio,
 of acrylic acid, of hexadecyl acrylate and of methyl acrylate in a 5/85/10 ratio,
 of acrylic acid and of polyoctadecyl (meth)acrylate in a 2.5/97.5 ratio.

It is also possible to use the polymer Structure "O" from National Starch, such as that described in document U.S. Pat. No. 5,736,125 with a melting point of 44° C.

The semi-crystalline polymers may in particular be semi-crystalline polymers with crystallizable pendent chains comprising fluoro groups, as described in Examples 1, 4, 6, 7 and 8 of document WO-A-01/19333.

It is also possible to use the semi-crystalline polymers obtained by copolymerization of stearyl acrylate and of acrylic acid or NVP as described, for example, in document U.S. Pat. No. 5,519,063 and more especially the product described in Example 1 of patent application EP 1 262 163, with a melting point, respectively, of 40° C.

It is also possible to use the semi-crystalline polymers obtained by copolymerization of behenyl acrylate and of acrylic acid or of NVP, as described in documents U.S. Pat. No. 5,519,063 and EP-A-0 550 745 and more especially those described in Examples 3 and 4 below, of polymer preparation.

The semi-crystalline polymers that are suitable for use in the invention may especially be Intelimer described in the document *Intelimers® polymers*, Landec IP22 (Rev. 4.97), with a melting point of 56° C., which is an impermeable, non-tacky product that is viscous at room temperature.

In particular, a semi-crystalline polymer that is suitable for preparing the compositions according to the present invention may be polystearyl acrylate, such as the product sold under the name Intelimer® IPA 13-1 from the company Air Products & Chemicals or Landec, or the polybehenyl acrylate sold under the name Intelimer® IPA 13-6 from the company Air Products & Chemicals or Landec.

Preferably, the amount of semi-crystalline polymer(s), preferably chosen from semi-crystalline polymers bearing crystallizable side chains, represents from 0.1% to 30% and better still from 0.1% to 20% by weight relative to the total weight of the composition. It preferably represents from 0.3% to 10% of the total weight of the composition.

The structuring or thickening of the fatty phase may advantageously be modulated as a function of the nature of the polymers and of their respective concentrations.

In particular, the amount of semi-crystalline polymer(s) is adjusted so as to afford the expected viscosity (in the case of a liquid composition) for the composition under consideration and as a function of the particular application envisaged.

B) Polymers Bearing in the Skeleton at Least One Crystallizable Block

This is also a case of polymers that are soluble or dispersible in the fatty phase by heating above their melting point mp. These polymers are especially block copolymers consisting of at least two blocks of different chemical nature, one of which is crystallizable.

The polymer bearing at least one crystallizable block in the backbone may be chosen from block copolymers of olefin or of cycloolefin containing a crystallizable chain, for instance those derived from the block polymerization of:

cyclobutene, cyclohexene, cyclooctene, norbornene (i.e. bicyclo(2,2,1)-2-heptene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene, or mixtures thereof, with ethylene, propylene, 1-butene, 3-methyl-1-butene, 1-hexene, 4-methyl-1-pentene, 1-octene, 1-decene or 1-eicosene, or mixtures thereof, and in particular copoly(ethylene/norbornene) blocks and (ethylene/propylene/ethylidene-norbornene) block terpolymers. Those resulting from the block copolymerization of at least two $C_2$-$C_{16}$, and better still $C_2$-$C_{12}$, α-olefins such as those mentioned above and in particular block bipolymers of ethylene and of 1-octene may also be used.

The polymer bearing at least one crystallizable block in the backbone may be chosen from copolymers containing at least one crystallizable block, the rest of the copolymer being amorphous (at room temperature). These copolymers can additionally exhibit two crystallizable blocks which are different in chemical nature.

The preferred copolymers are those that simultaneously contain at room temperature a crystallizable block and a lipophilic amorphous block that are sequentially distributed. Mention may be made, for example, of polymers containing one of the crystallizable blocks and one of the amorphous blocks below:

Block that is crystallizable by nature, of polyester type, for instance poly(alkylene terephthalate), or of polyolefin type, for instance polyethylenes or polypropylenes.

Amorphous and lipophilic block, for instance amorphous polyolefins or copoly(olefin)s such as poly(isobutylene), hydrogenated polybutadiene or hydrogenated poly(isoprene).

As examples of such copolymers containing a crystallizable block and an amorphous block, mention may be made of:

α) poly(ε-caprolactone)-b-poly(butadiene) block copolymers, preferably used hydrogenated, such as those described in the article D6 "Melting behavior of poly (caprolactone)-block-polybutadiene copolymers" from S, Nojima, Macromolecules, 32, 3727-3734 (1999), β) the hydrogenated block or multiblock poly(butylene terephthalate)-b-poly(isoprene) block copolymers cited in the article D7 "Study of morphological and mechanical properties of PP/PBT" by B. Boutevin et al., Polymer Bulletin, 34, 117-123 (1995), γ) the poly(ethylene)-b-copoly(ethylene/propylene) block copolymers cited in the articles D8 "Morphology of semi-crystalline block copolymers of ethylene-(ethylene-alt-propylene)" by P. Rangarajan et al., Macromolecules, 26, 4640-4645 (1993) and D9 "Polymer aggregates with crystalline cores: the system poly(ethylene)-poly(ethylene-propylene)" P. Richter et al., Macromolecules, 30, 1053-1068 (1997).

δ) the poly(ethylene)-b-poly(ethylethylene) block copolymers mentioned in the general article D10 "*Crystallization in block copolymers*" by I. W. Hamley, Advances in Polymer Science, vol. 148, 113-137 (1999).

C) Polycondensates of Aliphatic or Aromatic or Aliphatic/Aromatic Polyester Type The polyester polycondensates may be chosen from aliphatic polyesters. Their molecular mass is preferably greater than or equal to 200 and less than or equal to 10 000, and more preferably greater than or equal to 300 and less than or equal to 5000, preferably greater than or equal to 500 and greater than or equal to 2000 g/mol.

The polyester polycondensates are in particular chosen from polycaprolactones. In particular, the polycaprolactones may be chosen from ε-caprolactone homopolymers. The homopolymerization may be initiated with a diol, especially a diol containing from 2 to 10 carbon atoms, such as diethylene glycol, 1,4-butanediol or neopentyl glycol.

Polycaprolactones may be used for example, especially those sold under the names CAPA® 240 (melting point of 68° C. and molecular weight of 4000), 223 (melting point of 48° C. and molecular weight of 2000), 222 (melting point of 48° C. and molecular weight of 2000), 217 (melting point of 44° C. and molecular weight of 1250), 2125 (melting point of 45° C. and molecular weight of 1250), 212 (melting point of 45° C. and molecular weight of 1000), 210 (melting point of 38° C. and molecular weight of 1000), 205 (melting point of 39° C. and molecular weight of 830) by the company Solvay, or PCL-300 and PCL-700 by the company Union Carbide.

CAPA® 2125 whose melting point is between 35 and 45° C. and whose molecular weight is equal to 1250 may be used in particular.

The semi-crystalline polymers in the composition of the invention may or may not be partially crosslinked, provided that the degree of crosslinking does not interfere with their dissolution or dispersion in the fatty phase by heating above their melting point. It may then be a case of chemical crosslinking, by reaction with a multifunctional monomer during the polymerization. It may also be a case of physical crosslinking, which can then be due either to the establishment of bonds of hydrogen or dipolar type between groups carried by the polymer, such as, for example, dipolar interactions between carboxylate ionomers, these interactions being in low amount and carried by the backbone of the polymer; or to a phase separation between the crystallizable blocks and the amorphous blocks carried by the polymer.

Preferably, the semi-crystalline polymers of the composition according to the invention are noncrosslinked.

D) Copolymers of Ethylene and Propylene Prepared Via Metallocene Catalysis

The semi-crystalline polymer of the composition of the invention may also be a polymer obtained via metallocene catalysis, such as those described in patent US 2007/0 031 361. These polymers are copolymers of ethylene and propylene prepared via metallocene catalysis, i.e. by polymerization at low pressure and in the presence of a metallocene catalyst.

The weight-average mass (Mw) of these copolymers obtained via metallocene catalysis described in this document is less than or equal to 25 000 g/mol and ranges, for example, from 2000 to 22 000 g/mol and better still from 4000 to 20 000 g/mol.

The number-average mass (Mn) of these copolymers obtained via metallocene catalysis described in this document is preferably less than or equal to 15 000 g/mol and ranges, for example, from 1000 to 12 000 g/mol and better still from 2000 to 10 000 g/mol.

The polydispersity index I of the polymer is equal to the ratio of the weight-average mass Mw to the number-average mass Mn.

Preferably, the polydispersity index of the copolymers is between 1.5 and 10, preferably between 1.5 and 5, preferably between 1.5 and 3 and better still between 2 and 2.5.

The copolymers may be obtained in a known manner from ethylene and/or propylene monomers, for example via metallocene catalysis according to the process described in document EP 571 882. The copolymers of ethylene and propylene prepared via metallocene catalysis may be unmodified or "polar"-modified (i.e. modified such that they contain polar groups). The polar-modified copolymers may be prepared in a known manner from unmodified homopolymers and copolymers such as those described previously by oxidation with gases containing oxygen, such as air, or by grafting with polar monomers such as maleic acid or acrylic acid or alternatively derivatives of these acids. These two routes enabling polar modification of the polyolefins obtained via metallocene catalysis are described, respectively, in documents EP 890 583 and U.S. Pat. No. 5,998, 547.

According to the present invention, the polar-modified copolymers of ethylene and/or propylene prepared via metallocene catalysis that are particularly preferred are polymers modified such that they have hydrophilic properties. Examples that may be mentioned include ethylene and/or propylene homopolymers or copolymers modified by the presence of hydrophilic groups such as maleic anhydride, acrylate, methacrylate, polyvinylpyrrolidone (PVP), etc.

Ethylene and/or propylene homopolymers or copolymers modified by the presence of hydrophilic groups such as maleic anhydride or acrylate are particularly preferred. Examples that may be mentioned include:
polypropylene polymers modified with maleic anhydride (PPMA) sold by the company Clariant, or polypropylene-ethylene-maleic anhydride copolymers, such as those sold by the company Clariant under the name LicoCare, for instance LicoCare PP207 LP3349, LicoCare CM401 LP3345, LicoCare CA301 LP3346 and LicoCare CA302 LP3347.

In the context of a composition for the lips, a polar-modified polymer with a low degree of crystallinity, preferably of less than 40%, will be preferred.

Additives

A composition according to the invention may furthermore comprise any ingredient conventionally used as additive in cosmetics and dermatology.

These additives are advantageously chosen from antioxidants, thickeners, sweeteners, basifying agents, acidifying agents and preserving agents, and mixtures thereof.

According to a preferred embodiment, a composition in accordance with the invention comprises at least one of the additional compounds chosen from dyestuffs, hydrocarbon-based resins, dextrin esters, pasty fatty substances, film-forming polymers, hydrocarbon-based block copolymers, block ethylenic copolymers, organogelling agents, hydrocarbon-based polyamides, silicone polyamides, polyurethanes, semi-crystalline polymers, additional fillers, active agents, in particular moisturizing active agents such as glycerol, antioxidants, sweeteners, basifying or acidifying preserving agents, and mixtures thereof.

Needless to say, a person skilled in the art will take care to select this or these optional additional compound(s), and/or the amount thereof, such that the advantageous properties of the composition according to the invention are not, or are not substantially, adversely affected by the envisaged addition.

The composition according to the invention is in liquid form.

According to a second preferred embodiment, the composition is in liquid form, for example in the form of a lip gloss.

The term "liquid" means a fluid texture, i.e. which may especially be in creamy or pasty form. The compositions according to the invention may especially be in gloss form, intended for making up and/or caring for the skin or the lips. The term "liquid" especially means a composition that is not solid at 25° C., and whose viscosity it is possible to measure.

Protocol for Measuring the Viscosity:

The viscosity measurement is generally performed at 25° C., using a Rheomat RM180 viscometer equipped with a No. 4 spindle, the measurement being performed after 10 minutes of rotation of the spindle in the composition (after which time stabilization of the viscosity and of the spin speed of the spindle are observed), at a shear rate of 200 rpm.

Preferably, the composition has at 25° C. a viscosity of between 1 and 25 Pa·s and preferably between 2 and 20 Pa·s.

Preferably, the viscosity at 25° C. of a composition according to the invention is between 3 and 17 Pa·s.

The terms "between" and "ranging from" should be understood as including the limits.

The examples that follow are given as an illustration, without any limiting nature.

Unless otherwise mentioned, the values in the example below are expressed as % by weight relative to the total weight of the composition.

EXAMPLE 1

Lip Gloss

The composition below of liquid lip composition according to the invention was prepared. Composition 1 is a lip gloss according to the invention and comprises an oil, hydrophobic aerogel particles and a hydrocarbon-based resin.

| INCI US | Composition 1 according to the invention (weight %) |
|---|---|
| Silica silylate (Aerogel VM2270 from Dow Corning) | 1.5 |
| Synthetic wax (Cirebelle 108 from Cirebelle) | 1.5 |
| Yellow 6 Lake | 0.08 |
| Red 7 | 0.12 |
| Titanium dioxide | 0.24 |
| Isopropyl isostearate | 2.3 |
| Bis(diglyceryl) poly(2-acyladipate) (Softisan 649 from Sasol) | 7 |
| Octyldodecyl neopentanoate | 24 |
| Hydrogenated castor oil isostearate (Salacos HCISV-L from Nisshin Oillio) | 7 |
| Nacre | 1.8 |
| Fragrance | 0.05 |
| Hydrogenated polyisobutene (Parleam Lite from NOF Corporation) | 20.91 |
| Hydrogenated styrene/butadiene copolymer (Kraton G1657M from Kraton Polymers) | 7 |
| Hydrogenated styrene/methylstyrene/indene copolymer (Regalite R1100 from Eastman Chemical) | 15 |
| Hydrogenated polydecene (Puresyn 6 from Exxon Mobil Chemical) | 10 |
| Pentylene glycol | 1 |
| Caprylyl glycol | 0.5 |
| TOTAL | 100 |

Preparation Process

The compositions were obtained according to the following protocol:

In a first stage, the fillers and the pigments were ground in a three-roll mill in part of the oily phase (octyldodecyl neopentanoate and isopropyl isostearate, hydrogenated polyisobutene, hydrogenated polydecene).

In parallel, a pregel was prepared for the dispersion of the hydrocarbon-based resin and the hydrocarbon-based block copolymer in part of the octyldodecyl neopentanoate and hydrogenated polyisobutene oils. This pregel was introduced into a heating pan. The rest of the liposoluble ingredients were then mixed in the pan at a temperature of about 100° C. with stirring using a Rayneri blender, until a homogeneous mixture was obtained. The ground pigmentary material was then incorporated into the mixture, which was kept stirring until homogeneous.

Finally, the composition remained at room temperature for 24 hours before being conditioned in heating bags.

Evaluation of the Composition

Viscosity: the viscosity at 25° C. of the compositions was evaluated according to the protocol described previously.

Stability: the stability of the compositions is evaluated by storing the composition for 72 hours at room temperature and at 42° C. and by observing whether separation of the oily phase and/or sedimentation of the pigments and/or nacres takes place. The stability of the compositions was also evaluated after centrifugation at a speed of 450×g for 10 minutes.

Tack: the tacky nature of the deposits obtained with a composition was evaluated by applying the composition to the lips. The tack is evaluated 2 minutes after application by pressing the upper and lower lips together and evaluating the resistance to separation of the lips.

Gloss and migration: the gloss and the migration of the deposit obtained on the lips with composition 6 were evaluated using a Polka SEI-M-0216-POLK-02 polarimetric camera and a Chromosphere SEI-M-02232-CHRO-0 machine as described in patent application FR 2 829 344. The gloss is evaluated immediately after application and 1 hour after application of the formula. The formulation is applied to the lips of a panel of six individuals having fleshy and clear lips.

Application properties: the ease of applying the composition to the lips and especially the glidance on application are especially evaluated.

Results of the Evaluations
The results are as follows:

| PROPERTIES | Composition 1 according to the invention |
|---|---|
| Viscosity (Pa · s) | 12.5 |
| Stability 72 hours at room temperature | Yes |
| Stability 72 hours at 42° C. | Yes |
| Stability after centrifugation | Yes |
| Application property | Good: ease of application, good glidance, creamy composition and uniform deposit |
| Gloss of the deposit immediately after application | Very good T0 = 311 ± 20 |
| Gloss of the deposit 1 hour after application | Good =264 ± 17 |
| Migration | Non-migrating |
| Tack | Non-tacky |

Composition 1 is homogeneous and stable. In particular, no phase separation or sedimentation of the nacres and/or pigments is observed after 24 hours at room temperature or at 42° C. The stability was also tested after one month at 24° C. and after one month at 42° C., and the composition was always homogeneous, in the same way as after the centrifugation test.

The composition is easy to apply: it glides well over the lips when applied. Furthermore, the deposit obtained is creamy and comfortable, very glossy, non-tacky and non-migrating.

EXAMPLE 2

Liquid Lip Composition

The following liquid lip composition according to the invention was prepared. Composition 2 is a lip gloss and comprises an oil, hydrophobic aerogel particles and a hydrocarbon-based resin.

| NATURE | INCI NAME and COMMERCIAL REFERENCES | Composition 2 according to the invention (weight %) |
|---|---|---|
| Filler | Silica silylate (Aerogel VM-2270 from Dow Corning) | 1.5 |
| Polymer | Poly(C10-30 alkyl acrylate) (Intelimer IPA 13-1 from Air Products & Chemicals) | 0.5 |

-continued

| NATURE | INCI NAME and COMMERCIAL REFERENCES | Composition 2 according to the invention (weight %) |
|---|---|---|
| Silicone | Cetyl dimethicone (Abil Wax 9801 from Evonik Goldschmidt) | 1.5 |
| Dye | Red 7 | 0.1425 |
| Dye | Titanium dioxide | 0.616 |
| Dye | Blue 1 Lake | 0.0275 |
| Dye | Yellow 5 Lake | 0.224 |
| Dye | Yellow 6 Lake | 0.156 |
| Nacre | Nacres | 0.8 |
| Fatty substance | Bis(diglyceryl) poly(2-acyladipate) (Softisan 649 from Sasol) | 3.5 |
| Fatty substance | Octyldodecyl neopentanoate | 25.134 |
| Fatty substance | Hydrogenated castor oil isostearate (Salacos HCISV-L from Nisshin Oillio) | 3.5 |
| Fatty substance | Bis-behenyl/isostearyl/phytosteryl dimer dilinoleyl dimer dilinoleate (Plandool-G7 from Nippon Fine Chemical) | 3.5 |
| Polymer | Hydrogenated polyisobutene (Parleam Lite from NOF Corporation) | 12 |
| Polymer | Hydrogenated styrene/butadiene copolymer (Kraton G1657M from Kraton Polymers) | 5.6 |
| Polymer | Hydrogenated styrene/methylstyrene/indene copolymer (Regalite R1100 from Eastman Chemical) | 12 |
| Polymer | Hydrogenated polydecene (Puresyn 6 from Exxon Mobil Chemical) | 7.4 |
| Silicone | Trimethylsiloxyphenyl dimethicone (Belsil PDM 1000 from Wacker) | 21 |
| Active agent | Pentaerythrityl tetra-di-t-butyl hydroxyhydrocinnamate (Tinogard TT from BASF) | 0.1 |
| Solvent | Pentylene glycol | 0.5 |
| Solvent | Caprylyl glycol | 0.3 |
| | Total | 100% |

Preparation Protocol:

The composition was obtained according to the following protocol:

In a first stage, the fillers, the pigments and/or the active agents of phase were milled in a three-roll mill in part of the oily phase (octyldodecyl neopentanoate).

In parallel, a pure pregel was prepared by dispersing the hydrocarbon-based resin and the hydrocarbon-based copolymer in part of the oily phase (polydecene, polybutene, octyldodecyl neopentanoate). The pregel was placed in a heating pan.

The rest of the liposoluble ingredients were then added to the pan heated to a temperature of about 100° C. with stirring using a Rayneri blender, until a homogeneous mixture was obtained.

The ground pigmentary material was then incorporated into the mixture, which was kept stirring until homogeneous.

Finally, the composition was poured into heating bags and then placed at room temperature for 24 hours.

Evaluation of the Compositions

Viscosity: the viscosity at 25° C. of the compositions was evaluated according to the protocol described previously.

Stability: the stability of the composition was evaluated by storing the composition for 72 hours at room temperature, and at 42° C., and by observing whether separation of the oily phase and/or sedimentation of the pigments and/or nacres takes place. The stability of the compositions was also evaluated after centrifugation at a speed of 450×g for 10 minutes.

The stability of the composition was also evaluated after 1 month at room temperature and at 42° C.

Tack: the tacky nature of the deposits obtained with a composition was evaluated by applying the composition to the lips. The tack is evaluated 5 minutes after application by pressing the upper and lower lips together and evaluating the resistance to separation of the lips.

Gloss: the glossy nature of the deposits obtained with the compositions was evaluated in vivo by applying the composition to the lips. In particular, the gloss is evaluated immediately after application and 1 hour after application.

Transfer resistance: the transfer resistance of the deposit and especially of the colour of the deposit was tested by applying the composition to the lips and then, 5 minutes after application, by applying the lips to a white ceramic cup, as if preparing to drink from this cup. The transfer resistance is proportionately greater the weaker the colour intensity of the mark left by the lips on the cup.

Application properties: the ease of applying the composition to the lips and especially the glidance on application are especially evaluated.

The results are as follows:

| PROPERTIES | Composition 2 according to the invention |
|---|---|
| Viscosity (Pa · s) | 8.3 |
| Stability after 72 hours at room temperature | Yes |
| Stability after 72 hours at 42° C. | Yes |
| Stability after centrifugation | Yes |
| Application properties | Very good: ease of application, good glidance and uniform deposit |
| Gloss of the deposit immediately after application | Very good |
| Gloss of the deposit 1 hour after application | Very good |
| Transfer resistance | Good = little colour transfer |

Composition 2 is homogeneous and stable. In particular, no sedimentation of the nacres and/or pigments is observed after 72 hours at room temperature or at 42° C. The stability was also tested after 2 months at 24° C. and after 1 month at 42° C., and the composition was always homogeneous, in the same way as after the centrifugation test. The composition is easy to apply: it glides well over the lips on application. Furthermore, the deposit obtained is comfortable, glossy, sparingly tacky and has a good level of transfer resistance (good colour-transfer resistance).

EXAMPLE 3

Liquid Lip Composition

The following liquid lip composition according to the invention was prepared. Composition 3 is a lip gloss and comprises an oil, hydrophobic aerogel particles and a hydrocarbon-based resin.

| INCI NAME and COMMERCIAL REFERENCES | Composition 3 according to the invention |
| --- | --- |
| Hydrogenated polyisobutene (Parleam Lite from NOF Corporation) | 17.82 |
| Octyldodecyl neopentanoate | 21.12 |
| Isopropyl isostearate | 1.95 |
| Hydrogenated castor oil isostearate (Salacos HCISV-L from Nisshin Oillio) | 5.95 |
| Bis-(diglyceryl poly(2-acyladipate) Softisan 649 from Sasol) | 5.95 |
| Hydrogenated styrene/butadiene copolymer (Kraton G1657M from Kraton Polymers) | 6.46 |
| Hydrogenated styrene/methylstyrene/indene copolymer (Regalite R1100 from Eastman Chemical) | 13.84 |
| Red 7 | 0.24 |
| Iron oxide | 0.07 |
| Mica (and) iron oxides | 1.50 |
| Silica silylate (aerogel VM-2270 from Dow Corning) | 2 |
| Dimethicone (Xiameter PMX-200 Silicone Fluid 350CS from Dow Corning) | 7.5 |
| Dimethicone (Xiameter PMX-200 Silicone Fluid 100CS from Dow Corning) | 7.5 |
| Hydrogenated polydecene (Puresyn 6 from ExxonMobil Chemical) | 8.55 |
| TOTAL | 100 |

Composition 3 was prepared and evaluated as described for the composition.

Results of the Evaluation

| PROPERTIES | Composition 3 according to the invention |
| --- | --- |
| Viscosity (in Pa · s) | 8.6 |
| Stability after 72 hours at 24° C. | Stable |
| Stability after 72 hours at 42° C. | Stable |
| Application properties | Very good: easy application, good glidance and homogeneous deposit |
| Gloss of the deposit immediately after application | Very good |
| Tack | Sparingly tacky |
| Transfer resistance | Good = little colour transfer |

Composition 3 according to the invention is homogeneous and stable. It has good application properties (glidant and creamy). The deposit obtained is homogeneous, glossy, sparingly tacky and has good colour-transfer resistance.

EXAMPLE 4

Liquid Lip Composition

Example 4a

Preparation of a Poly(Isobornyl Acrylate/Isobornyl Methacrylate/Isobutyl Acrylate/Acrylic Acid) Copolymer 300 g of isododecane are placed in a 1-litre reactor and the temperature is then raised to go from room temperature (25° C.) to 90° C. over 1 hour.

105 g of isobornyl methacrylate, 105 g of isobornyl acrylate and 1.8 g of 2,5-bis(2-ethylhexanoylperoxy)-2,5-dimethylhexane (Trigonox® 141 from Akzo Nobel) are then added, at 90° C. and over 1 hour.

The mixture is maintained at 90° C. for 1 hour 30 minutes.

75 g of isobutyl acrylate, 15 g of acrylic acid and 1.2 g of 2,5-bis(2-ethylhexanoylperoxy)-2,5-dimethylhexane are then added to the preceding mixture, still at 90° C. and over 30 minutes.

The mixture is maintained at 90° C. for 3 hours and is then cooled.

A solution is thus obtained containing 50% copolymer solids in 50% isododecane comprising a first poly(isobornyl acrylate/isobornyl methacrylate) block with a Tg of 128° C., a second poly(isobutyl acrylate/acrylic acid) block with a Tg of −9° C. and an intermediate block which is an isobornyl acrylate/isobornyl methacrylate/isobutyl acrylate/acrylic acid statistical copolymer.

The Tg of the copolymer is 74° C.

These are theoretical Tg values calculated by Fox's law.

Example 4b

Distillation of the Synthesis Solvent (Isododecane) by Adding Octyldodecyl Neopentanoate The solution obtained in Example 1 is heated to 130° C. under a vacuum of 100 mbar to evaporate off the isododecane while simultaneously adding octyldodecyl neopentanoate. The isododecane is entirely replaced by the same weight amount of octyldodecyl neopentanoate.

The use of octyldodecyl neopentanoate makes it possible to evaporate off all the isododecane, which remains, if at all, only in residual trace amounts. A solution containing 50% copolymer solids in 50% octyldodecyl neopentanoate is thus obtained.

Example 4c

Liquid Lip Composition

The liquid lip composition 3c below according to the invention was prepared. Composition 4c is a lip gloss and comprises an oil, hydrophobic aerogel particles and a wax with a melting point of greater than or equal to 60° C., and a block ethylenic polymer as prepared in Examples 4a and 4b.

| Compounds | Formula 4c according to the invention (weight %) |
| --- | --- |
| Silica silylate (Aerogel VM2270 from Dow Corning) | 2.5 |
| Synthetic wax (Cirebelle 108 from Cirebelle) | 0.25 |

| Compounds | Formula 4c according to the invention (weight %) |
|---|---|
| Polymethylsilsesquioxane (Tospearl 145 A from Momentive Performance Materials) | 1 |
| Acrylic acid/isobutyl acrylate/isobornyl acrylate copolymer (at 50% in octyldodecyl neopentanoate), as prepared in Example 4a) | 5 |
| Acrylic acid/isobutyl acrylate/isobornyl acrylate copolymer (at 50% in isododecane), as prepared in Example 4b) | 25 |
| Hydrogenated styrene/methylstyrene/indene copolymer (Regalite R1100 from Eastman Chemical) | 3.52 |
| Caprylic/capric glyceride (Capmul MCM from Abitec) | 2 |
| Polybutene (Indopol H 100 from Ineos) | 10.65 |
| Squalane (Pripure 3759 from Croda) | 8.18 |
| Trimethylsiloxyphenyl dimethicone (Wacker-Belsil PDM 1000 from Wacker) | 25.03 |
| Octyldodecanol | 12.107 |
| Caprylyl glycol | 0.05 |
| Iron oxides | 0.1 |
| Red 7 | 0.2 |
| Red 28 Lake | 0.399 |
| Yellow 6 Lake | 0.064 |
| Nacres | 5 |
| Total | 100 |

Preparation Method:

In a first stage, the pigments were milled in the octyldodecyl neopentanoate.

The waxes were heated to a temperature of 95-98° C., along with the fillers and the block ethylenic copolymer in a heating pan with stirring using a Rayneri blender.

The hydrocarbon-based resin was dissolved in part of the oily phase. The ground pigmentary material and the mixture of molten waxes were added to the hydrocarbon-based resin and the mixture was kept stirring using a Rayneri blender. The phenyl silicone oil and the isododecane were then added to the mixture, with continued stirring using a Rayneri blender, until homogeneous.

Finally, the mixture was poured into isododecane-leaktight heating bags and then placed at room temperature for 24 hours.

Evaluation of the Compositions

Viscosity: the viscosity at 25° C. of the composition was evaluated according to the protocol described previously.

Stability: the stability of the compositions is evaluated by storing the composition at room temperature for 72 hours, and at 42° C. for 72 hours and by observing whether separation of the oily phase and/or sedimentation of the pigments and/or nacres takes place. The stability of the compositions is also evaluated after centrifugation at a speed of 450 g for 10 minutes.

Tack: the tacky nature of the deposits obtained with a composition was evaluated by applying the composition to the lips. The tack is evaluated 2 minutes after application by pinching together the upper and lower lips and evaluating the resistance to separation of the lips.

Gloss: the glossy nature of the deposits obtained with the compositions was evaluated in vivo, by applying the composition to the lips. In particular, the gloss is evaluated immediately after application, and also 1 hour after application.

Application properties: the ease of application of the composition to the lips and especially the glidance on application are evaluated.

Results of the Evaluations

| Properties | Composition 4c according to the invention |
|---|---|
| Viscosity (Pa · s) | 8.3 |
| STABILITY after 72 hours at room temperature | Stable |
| STABILITY after 72 hours at 42° C. | Stable |
| STABILITY after centrifugation | Stable |
| GLOSS of the deposit immediately after application | Good |
| Application properties | Good: easy application, good glidance and homogeneous deposit |
| Tack | Sparingly tacky |

Composition 4c above according to the invention is stable, after 72 hours at room temperature and also at 42° C., and also after centrifugation. In particular, no phase separation of the oily phase or sedimentation of the nacres and/or pigments to the bottom of the heating bag is observed.

Moreover, the composition applies easily to the lips: it glides well and spreads easily and produces a thin, homogeneous deposit. Furthermore, the deposit obtained is glossy and sparingly tacky.

The invention claimed is:

1. A composition comprising, in a physiologically acceptable medium, at least one fatty phase comprising:
   an oil;
   hydrophobic silica aerogel particles; and
   a hydrocarbon-based indene resin;
   wherein the composition comprises less than 5% by weight of water relative to the total weight of the composition.

2. The composition according to claim 1, wherein the hydrophobic silica aerogel particles have a specific surface area per unit of mass ($S_M$) ranging from 500 to 1500 m²/g and a size expressed as the volume-mean diameter (D[0.5]) ranging from 1 to 1500 μm.

3. The composition according to claim 1, wherein the hydrophobic aerogel particles have an oil absorption capacity, measured at the wet point, ranging from 5 to 18 ml/g of the particles.

4. The composition according to claim 1, wherein the hydrophobic aerogel particles have a tapped density ranging from 0.02 g/cm³ to 0.10 g/cm³.

5. The composition according to claim 1, wherein the hydrophobic silica aerogel particles are hydrophobic silica aerogel particles that are surface-modified with trimethylsilyl groups.

6. The composition according to claim 1, wherein the hydrophobic aerogel particles are present in an active material content ranging from 0.1% to 15% by weight, relative to the total weight of the composition.

7. The composition according to claim 1, wherein the hydrocarbon-based indene resin is selected from hydrogenated indene/methylstyrene/styrene copolymers.

8. The composition according to claim 1, wherein the hydrocarbon-based indene resin is present in a content ranging from 1% to 45% by weight, relative to the total weight of the composition.

9. The composition according to claim 1, wherein the composition comprises at least one hydrocarbon-based block copolymer.

10. The composition according to claim 9, wherein the hydrocarbon-based block copolymer comprises at least one styrene block and at least one block comprising units selected from the group consisting of butadiene, ethylene, propylene, butylene, isoprene, hydrogenated diblock copolymers of styrene-ethylene/propylene, of styrene-ethylene/ butadiene and of styrene-ethylene/butylene, hydrogenated triblock copolymers of styrene-ethylene/butadiene-styrene, of styrene-butylene/ethylene-styrene, of styrene-isoprene-styrene and of styrene-butadiene-styrene, and mixtures thereof.

11. The composition according to claim 9, wherein the hydrocarbon-based block copolymer is a mixture of a styrene-butylene/ethylene-styrene triblock hydrogenated copolymer and a styrene-ethylene/butylene diblock copolymer.

12. The composition according to claim 9, wherein the hydrocarbon-based block copolymer is present in the composition in a content ranging from 0.1% to 15% by weight relative to the total weight of the composition.

13. The composition according to claim 1, wherein the composition comprises at least one wax.

14. The composition according to claim 13, wherein the composition comprises a total content of the wax ranging from 0.1% to 15% by weight, relative to the total weight of the composition.

15. The composition according to claim 1, wherein the oil is a non-volatile oil selected from the group consisting of:
hydrocarbon-based oils selected from apolar hydrocarbon-based oils selected from the group consisting of polybutenes, polyisobutenes, hydrogenated polyisobutenes, polydecenes, hydrogenated polydecenes, and mixtures thereof, and polar hydrocarbon-based oils selected from the group consisting of hydrocarbon-based oils from plants or of plant origin, ester oils, fatty alcohols comprising 12 to 26 carbon atoms, fatty acids comprising 12 to 26 carbon atoms and vinylpyrrolidone copolymers, and mixtures thereof,
silicone oils selected from the group consisting of linear or branched polydimethylsiloxanes, non-volatile polydimethylsiloxanes and/or polydimethylsiloxanes comprising alkyl, alkoxy or phenyl groups, which are pendent or at the end of the silicone chain, these groups comprising 2 to 24 carbon atoms,
fluoro oils,
and mixtures thereof.

16. The composition according to claim 15, wherein the total content of the non-volatile oil ranges from 15% to 90% by weight, relative to the total weight of the composition.

17. The composition according to claim 1, wherein the composition is free of nanometric-sized silica.

18. The composition according to claim 1, wherein the composition is free of hydrophobic-treated fumed silica.

19. The composition according to claim 1, wherein the composition comprises at least one additional compound selected from the group consisting of dyestuffs, dextrin esters, pasty fatty substances, film-forming polymers, block ethylenic copolymers, organogelling agents, hydrocarbon-based polyamides, silicone polyamides, polyurethanes, semi-crystalline polymers, additional fillers, active agents, and mixtures thereof.

20. The composition according to claim 1, wherein the composition comprises at least one dyestuff selected from the group consisting of pigments and/or nacres, and mixtures thereof.

21. The composition according to claim 1, wherein the composition is in liquid form at room temperature.

22. The composition according to claim 1, wherein the composition is incorporated in a product for making up the skin and/or the lips.

23. A process for making up and/or caring for the skin and/or the lips, comprising applying to the skin and/or the lips, the composition according to claim 1.

24. The composition according to claim 1, wherein the hydrocarbon-based indene resin is hydrogenated.

25. The composition according to claim 1, wherein the hydrocarbon-based indene resin is derived from the polymerization of indene monomer and of at least one monomer selected from the group consisting of styrene, methylindene and methylstyrene.

26. The composition according to claim 1, wherein the oil is a non-volatile oil.

* * * * *